(12) United States Patent
Kinoshita et al.

(10) Patent No.: US 8,818,732 B2
(45) Date of Patent: Aug. 26, 2014

(54) MOLECULAR NETWORK ANALYSIS SUPPORT METHOD AND APPARATUS

(75) Inventors: Shuhei Kinoshita, Kawasaki (JP); Kentaro Doi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1312 days.

(21) Appl. No.: 12/508,039

(22) Filed: Jul. 23, 2009

(65) Prior Publication Data

US 2010/0010747 A1    Jan. 14, 2010

Related U.S. Application Data

(63) Continuation of application No. PCT/JP2008/052149, filed on Feb. 8, 2008.

(30) Foreign Application Priority Data

Feb. 23, 2007 (JP) ................................. 2007-044456

(51) Int. Cl.
*G06F 19/00* (2011.01)
*G06F 19/12* (2011.01)

(52) U.S. Cl.
CPC ..................................... *G06F 19/12* (2013.01)
USPC .......................................................... 702/19

(58) Field of Classification Search
None
See application file for complete search history.

(56) References Cited

U.S. PATENT DOCUMENTS

| 2002/0004792 A1 | 1/2002 | Busa |
| 2005/0080773 A1 | 4/2005 | Koike |
| 2006/0004706 A1 | 1/2006 | Tomioka |
| 2006/0106544 A1 | 5/2006 | Ohta |
| 2007/0022182 A1 | 1/2007 | Ihara |

FOREIGN PATENT DOCUMENTS

| JP | 2003-186894 | 7/2003 |
| JP | 2005-122231 | 5/2005 |
| JP | 2006-146380 | 6/2006 |
| WO | 03/077159 | 9/2003 |
| WO | 2005/096207 | 10/2005 |

OTHER PUBLICATIONS

International Preliminary Report on Patentability, mailed Sep. 3, 2009, in corresponding International Application No. PCT/JP2008/052149 (6 pp.).
Extended European Search Report issued Oct. 25, 2012 in corresponding European Patent Application No. 08711028.4.
Tor-Kristian Jenssen et al., "A literature network of human genes for high-throughput analysis of gene expression", Nature Genetics, vol. 28, May 2001, pp. 21-28.
Blaise TF Alako et al., "CoPub Mapper: mining MEDLINE based on search term co-publication", BMC Bioinformatics 2005, Mar. 2005, pp. 1-15.
English Translation of the International Preliminary Report on Patentability mailed Nov. 19, 2009 in corresponding International Patent Application PCT/JP2008/052149.
"PubMed" [online],URL:http://www.ncbi.nlm.nih.gov/entrez/query.fcgi, p. 1/1, retrieved Dec. 25, 2006.
"KEGG:Kyoto Encyclopedia of Genes and Genomes" [online], URL:http://www.genome.jp/kegg/pathway.html, pp. 1/7-7/7, retrieved Dec. 25, 2006.
"BioCarta" [online], URL:http://www.biocarta.com/, p. 1/1, retrieved Dec. 25, 2006.
"MeSH"[online], URL:http://www.nlm.nih.gov/mesh/meshhome.html, p. 1/1, retrieved Dec. 25, 2006.
"OMIMI" [online], URL:http://www.ncbi.nlm.nih.gov/entrez/query._fcgi?db=OMIM, p. 1/1, retrieved Dec. 26, 2006.
"H-invDB" [online], URL: http://www.jbic.or.jp/activity/i_db_pj/h-inv_db.html, p. 1/1, retrieved Dec. 26, 2006.
"H-invDB" [online] http://www.h-invitational.jp/, pp. 1/2 and 2/2, retrieved Dec. 26, 2006.
"H-invDB" [online] http://www.h-invitational.jp/hinv/ahg=db/index.jsp, p. 1/1, retrieved Dec. 26, 2006.
"BMC Bioinformatics." 2005-6 Suppl 1 S4.Epub,[online], URL: http://mwv.biomedc entral.com/1471-2105/6/S1/S4, pp. 1/6-6/6, May 24, 2005.
"BioCreAtIvE" [online], URL:http://biocreative.sourceforge.net/, pp. 1/2 and 2/2, retrieved Dec. 25, 2006.
"Human Protein Reference Database" [online],URL:http://www.hprd.org/, pp. 1/2 and 2/2, retrieved Jan. 16, 2007.
BIND [online], URL:http://www.blueprintorg/, p. 1/1, retrieved Jan. 16, 2007.

*Primary Examiner* — Lori A Clow
(74) *Attorney, Agent, or Firm* — Staas & Halsey LLP

(57) ABSTRACT

A molecular network analysis support method includes receiving designation of a biological phenomenon, extracting an interaction from a molecular network, and calculating a relation strength between the designated biological phenomenon and the extracted interaction.

18 Claims, 28 Drawing Sheets

FIG.2

MEDICAL REFERENCES DB 200

| REFERENCE ID | TITLE | ABSTRACT | AUTHOR | DATE OF PUBLICATION | MeSH TERM |
|---|---|---|---|---|---|
| 12235730 | Therapeutische Umschau. Revue therapeutique | The major risk factor for the development of insulin resistance and type 2 diabetes is obesity. A key role is ... | Stockli R, Keller U. | 2002 Aug | Adipose Tissue<br>Diabetes Mellitus<br>Diabetes Mellitus, Type 2<br>Energy Metabolism<br>Humans<br>Insulin Resistance<br>Obesity<br>Risk Factors |
| 15725700 | Nuclear receptors as targets for drug development: crosstalk between ... | Peroxisome proliferator-activated receptor gamma (PPARgamma) is a ligand-dependent nuclear receptor and regulates adipogenesis and fat metabolism. PPARgamma is activated by ... | Takada I, Suzawa M, Kato S. | 2005 Feb | Animals<br>Bone Marrow Cells<br>Cytokines<br>Drug Delivery Systems<br>Humans<br>Mesenchymal Stem Cells<br>PPAR gamma<br>Pharmaceutical Preparations<br>Receptor Cross-Talk |
| 15877288 | Peroxisome proliferator-activated receptor-gamma agonist rosiglitazone reduces clinical ... | Rosiglitazone, an agonist of peroxisome proliferator-activated receptor-gamma (PPAR gamma), is an insulin-sensitizing antidiabetic agent and inhibits restenosis in animal blood vessels. However ... | Wang G, Wei J, Guan Y, Jin N, Mao J, Wang X. | 2005 May | Aged<br>Angioplasty, Transluminal, Percutaneous Coronary<br>C-Reactive Protein<br>Chemokine CCL2<br>Chemokines<br>Coronary Disease<br>Diabetes Mellitus, Type 2<br>Diabetic Angiopathies |
| ... | ... | ... | ... | ... | ... |

FIG.3

INTERACTION DB 300

| MOLECULE A | | MOLECULE B | | REFERENCE ID | INTERACTION TYPE | INTERACTION DIRECTION |
|---|---|---|---|---|---|---|
| STANDARD MOLECULAR NOTATION | MOLECULE TYPE | STANDARD MOLECULAR NOTATION | MOLECULE TYPE | | | |
| PPARG | PROTEIN | TNF | PROTEIN | 15725700 | INHIBITION | ↓ |
| PPARG | PROTEIN | IL1 | PROTEIN | 15725700 | INHIBITION | ↓ |
| TNF | PROTEIN | PPARG | PROTEIN | 15563986 | INHIBITION | ↑ |
| PPARG | PROTEIN | ADIPOQ | PROTEIN | 12235730 | ADJUSTMENT | ↓ |
| PPARG | PROTEIN | NCOA1 | PROTEIN | 16171942 | BONDING | NO DIRECTION |
| PPARG | PROTEIN | pioglitazone | COMPOUND | 16039276 | ACTIVATION | ↓ |
| rosiglitazone | COMPOUND | PPARG | PROTEIN | 15877288 | ACTIVATION | ↑ |
| ... | ... | ... | ... | ... | ... | ... |

FIG.4

PHARMACOLOGY DB — 400

| ID | STANDARD MOLECULAR NOTATION | BIOLOGICAL PHENOMENON | RELATED DESCRIPTION |
|---|---|---|---|
| OMIM: *601487 | PPARG | Diabetes Mellitus, Type 2 | In 4 of 121 obese subjects, Ristow et al. (1998) identified a missense mutation in the PPARG2 gene (601487.0001). None of 237 subjects of normal weight had the mutation. All the subjects with the mutant allele were markedly obese. ... |
| OMIM: *601487 | PPARG | Colonic Neoplasms | In a sporadic colon cancer (114500) tumor, Sarraf et al. (1999) identified a somatic 1-bp deletion (472delA) in the PPARG gene. ... |
| ... | ... | ... | ... |

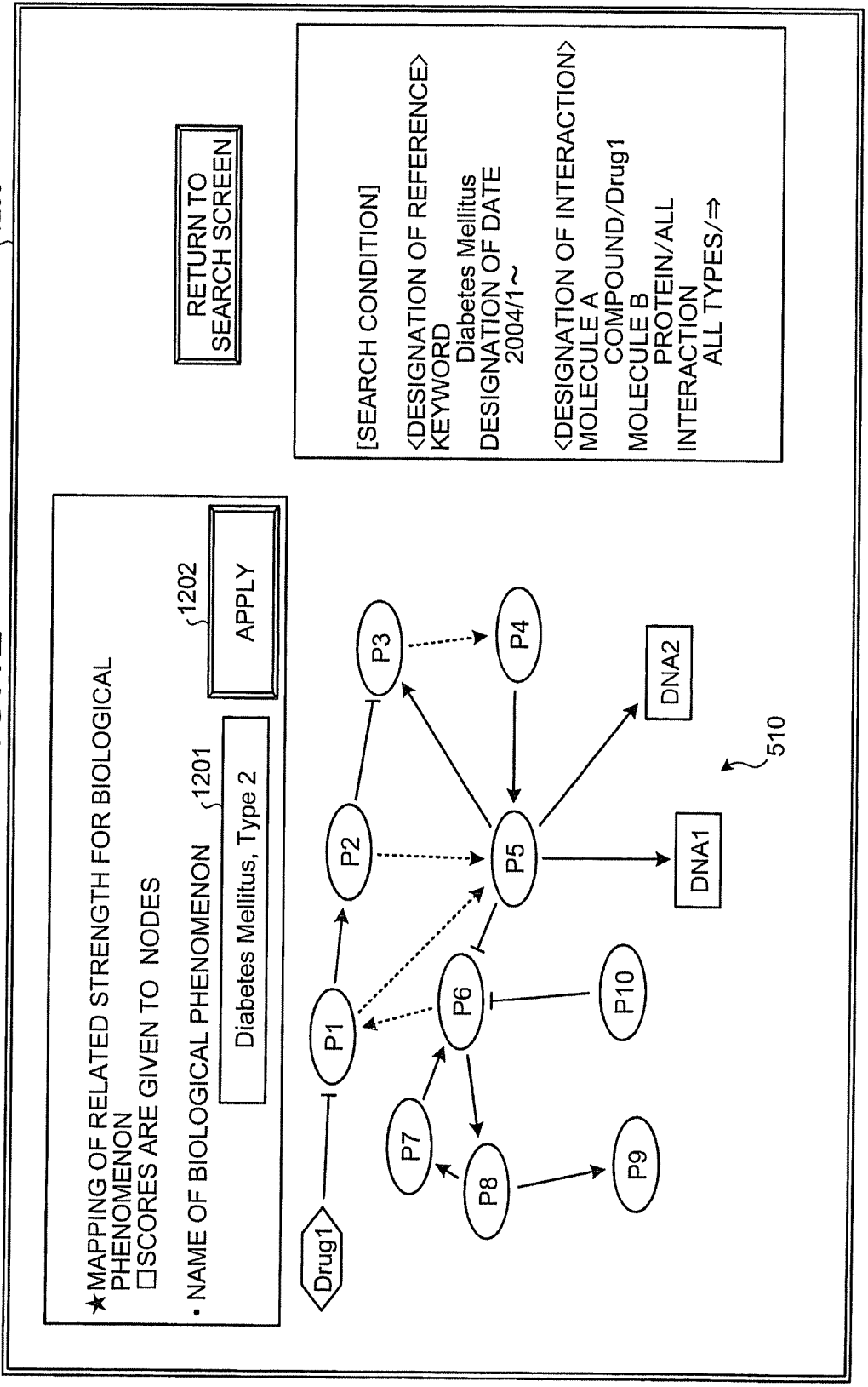

FIG.13

| MOLECULE A | | MOLECULE B | | REFER-ENCE ID | INTER-ACTION TYPE | INTER-ACTION DIREC-TION | DIRECT BONDING | RELATION STRENGTH S1 | CORRE-SPOND-ING COLOR |
|---|---|---|---|---|---|---|---|---|---|
| STANDARD MOLECULAR NOTATION | MOLECULE TYPE | STANDARD MOLECULAR NOTATION | MOLECULE TYPE | | | | | | |
| Drug1 | COMPOUND | P1 | PROTEIN | 23456 56789 | INHIBITION | ↑ | BONDING | 12.34 | RED |
| P1 | PROTEIN | P2 | PROTEIN | 123456 345678 ... | ACTIVATION | ↑ | BONDING | 6.37 | BLUE |
| P5 | PROTEIN | P1 | PROTEIN | 123456 45234 ... | ACTIVATION | ↓ | NO DATA | 2.18 | BLACK |
| P2 | PROTEIN | P3 | PROTEIN | 13456 529924 ... | INHIBITION | ↑ | BONDING | 8.77 | PINK |
| P5 | PROTEIN | P2 | PROTEIN | 424427 | ACTIVATION | ↓ | NO BONDING | 1.33 | BLACK |
| ... | ... | ... | ... | ... | ... | ... | ... | ... | ... |

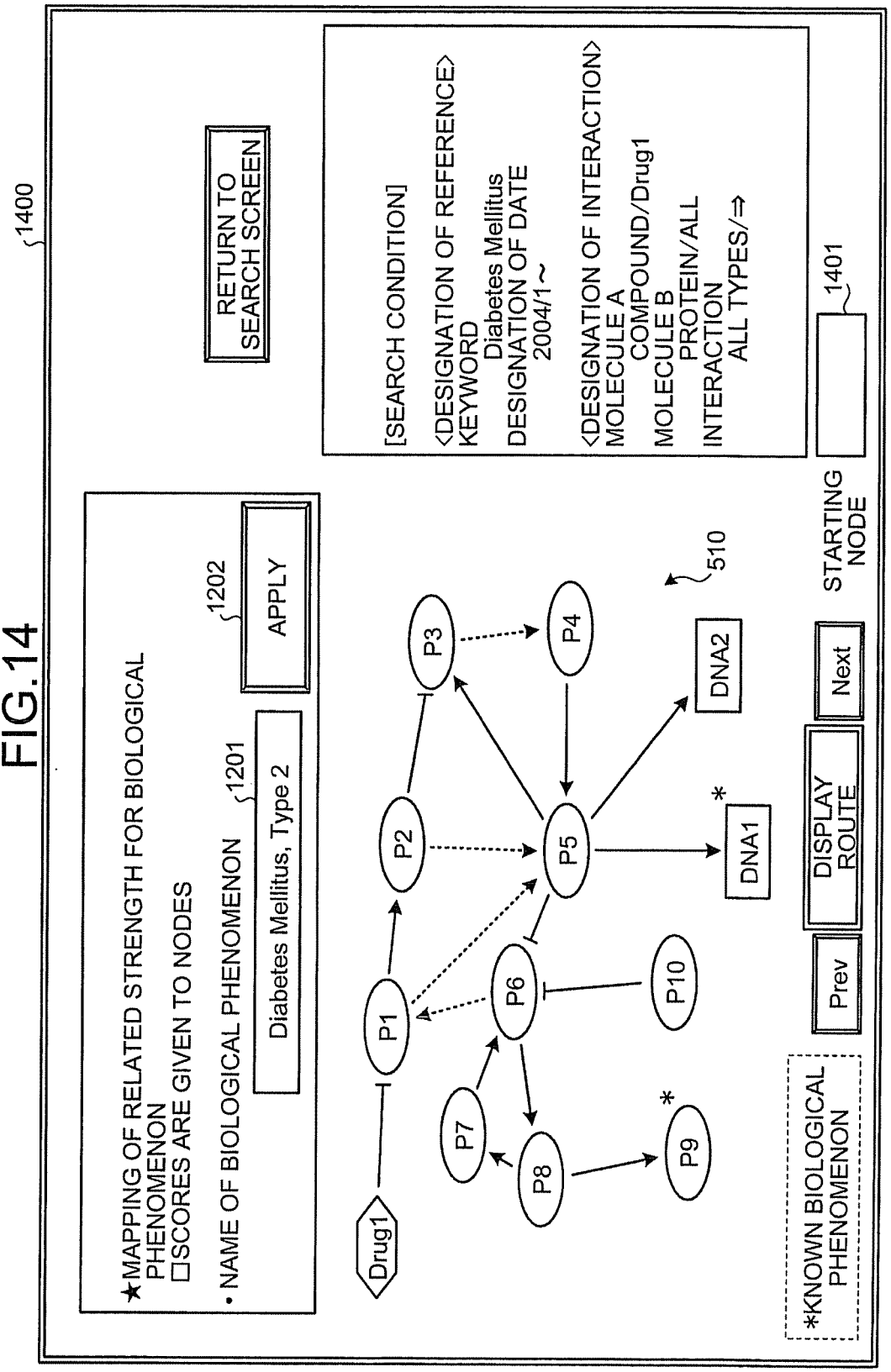

| STANDARD MOLECULAR NOTATION | MOLECULE TYPE | RELATION STRENGTH S2 | CORRESPONDING COLOR |
|---|---|---|---|
| Drug1 | COMPOUND | 2.18 | BLACK |
| P4 | PROTEIN | 7.89 | PINK |
| P5 | PROTEIN | 9.14 | PINK |
| P2 | PROTEIN | 28.35 | RED |
| P9 | PROTEIN | 35.44 | RED |
| ⋮ | ⋮ | ⋮ | ⋮ |

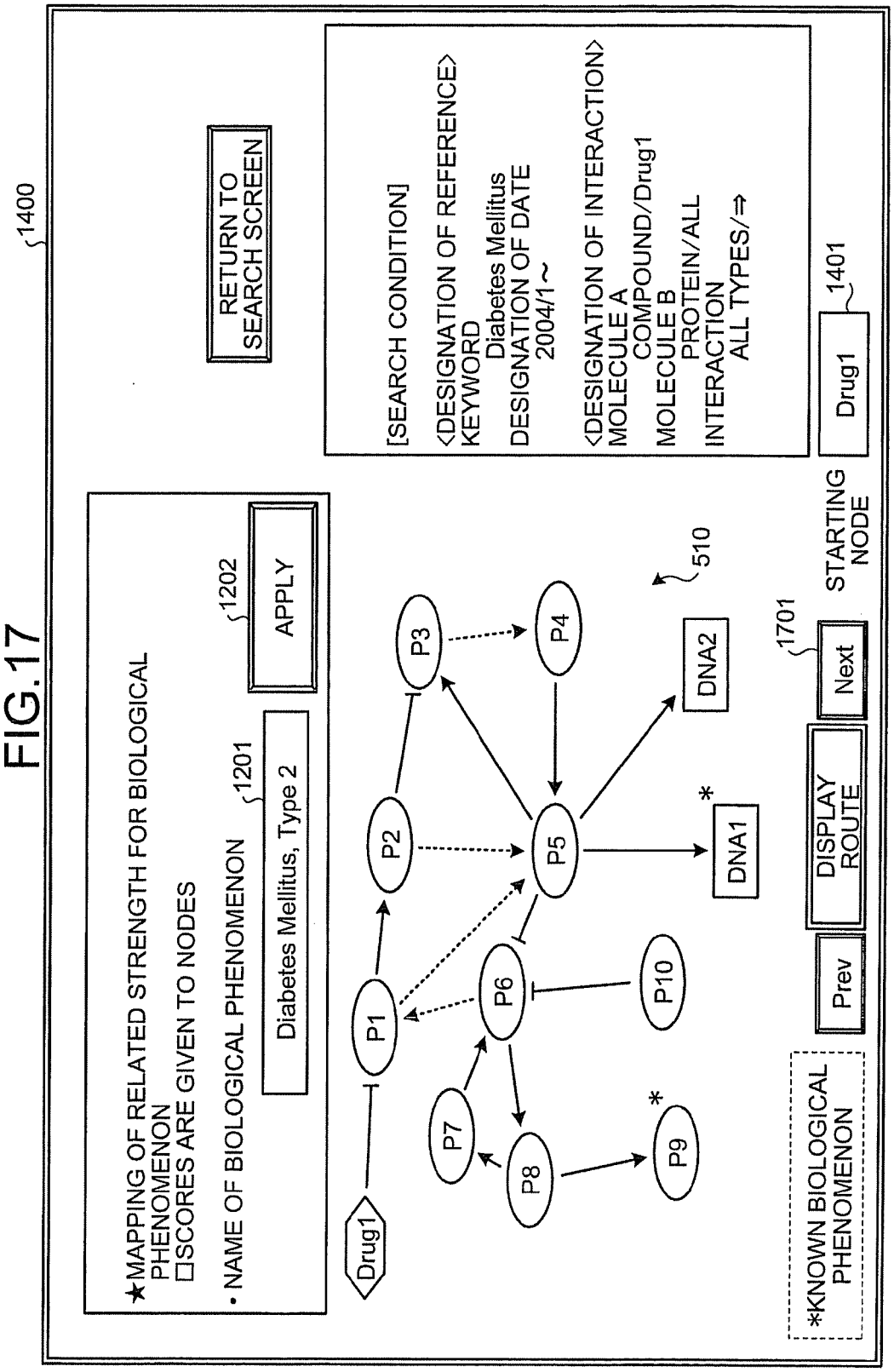

FIG.18

Table 1110:

| ROUTE ID | STARTING NODE | | ENDING NODE | | RETRIEVED ROUTE | RELATION STRENGTH S3 OF RETRIEVED ROUTE |
|---|---|---|---|---|---|---|
| | STANDARD MOLECULAR NOTATION | MOLE-CULE TYPE | STANDARD MOLECULAR NOTATION | MOLE-CULE TYPE | | |
| 001 | Drug1 | COMPOUND | DNA1 | GENE | Drug1→P1→P5→DNA1 | 4.52 |
| 002 | Drug1 | COMPOUND | P9 | PROTEIN | Drug1→P1→P5→P6→P8→P9 | 2.56 |
| 003 | Drug1 | COMPOUND | DNA1 | GENE | Drug1→P1→P2→P3→P4→P5→DNA1 | 10.83 |
| 004 | Drug1 | COMPOUND | DNA1 | GENE | Drug1→P1→P2→P5→DNA1 | 1.42 |
| 005 | Drug1 | COMPOUND | P9 | PROTEIN | Drug1→P1→P2→P5→P6→P8→P9 | 5.14 |
| 006 | Drug1 | COMPOUND | P9 | PROTEIN | Drug1→P1→P2→P3→P4→P5→P6→P8→P9 | 6.42 |

⇩ SORTING

Table 1800:

| ROUTE ID | STARTING NODE | | ENDING NODE | | RETRIEVED ROUTE | RELATION STRENGTH S3 OF RETRIEVED ROUTE | RANK |
|---|---|---|---|---|---|---|---|
| | STANDARD MOLECULAR NOTATION | MOLE-CULE TYPE | STANDARD MOLECULAR NOTATION | MOLE-CULE TYPE | | | |
| 003 | Drug1 | COMPOUND | DNA1 | GENE | Drug1→P1→P2→P3→P4→P5→DNA1 | 10.83 | 1 |
| 006 | Drug1 | COMPOUND | P9 | PROTEIN | Drug1→P1→P2→P3→P4→P5→P6→P8→P9 | 6.42 | 2 |
| 005 | Drug1 | COMPOUND | P9 | PROTEIN | Drug1→P1→P2→P5→P6→P8→P9 | 5.14 | 3 |
| 001 | Drug1 | COMPOUND | DNA1 | GENE | Drug1→P1→P5→DNA1 | 4.52 | 4 |
| 002 | Drug1 | COMPOUND | P9 | PROTEIN | Drug1→P1→P5→P6→P8→P9 | 2.56 | 5 |
| 004 | Drug1 | COMPOUND | DNA1 | GENE | Drug1→P1→P2→P5→DNA1 | 1.42 | 6 |

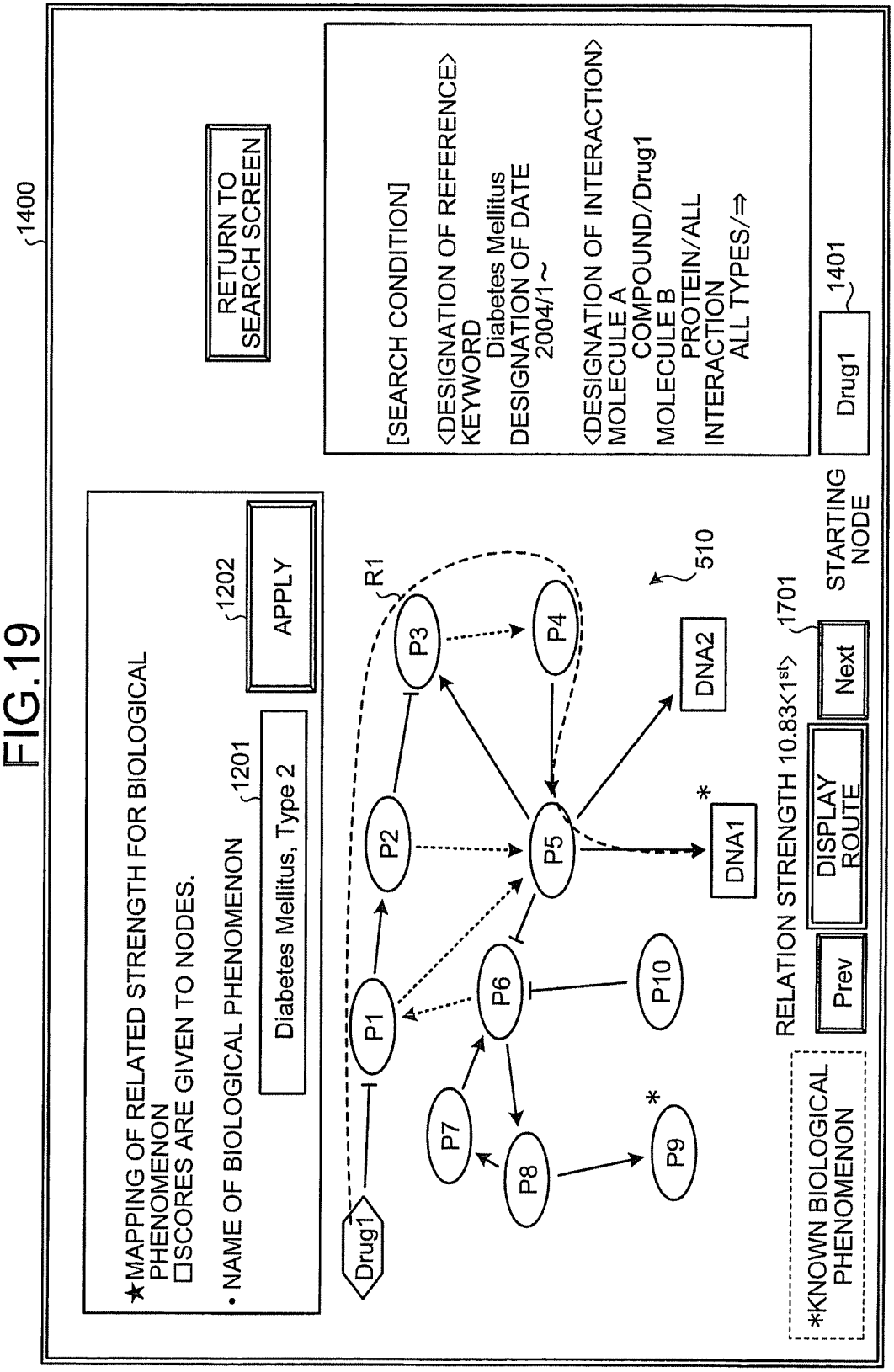

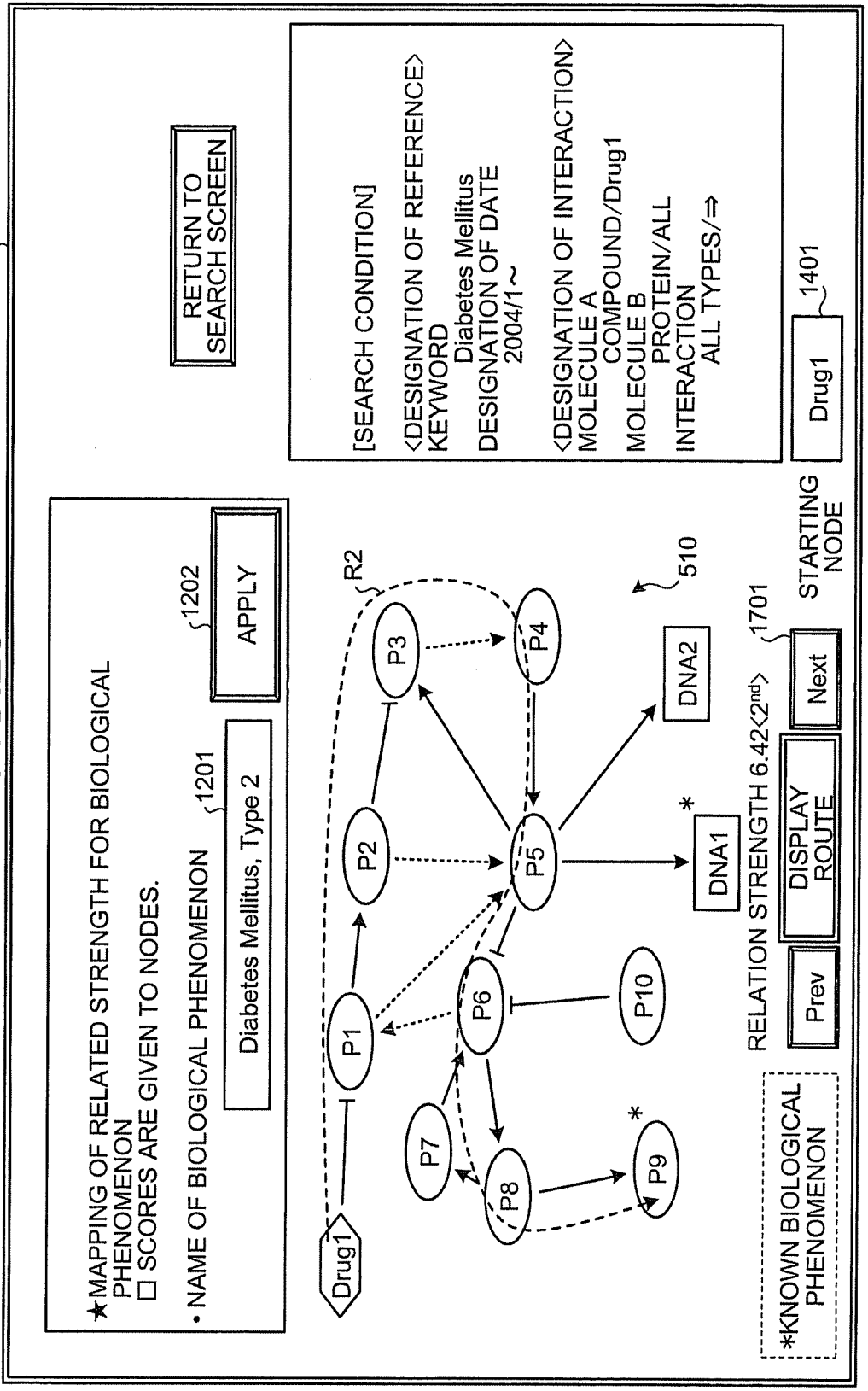

FIG.21

| ROUTE ID | MOLECULE A | | MOLECULE B | | RETRIEVED ROUTE | RELATION STRENGTH S3 OF RETRIEVED ROUTE | RANK |
|---|---|---|---|---|---|---|---|
| | STANDARD MOLECULAR NOTATION | MOLE-CULE TYPE | STANDARD MOLECULAR NOTATION | MOLE-CULE TYPE | | | |
| 006 | Drug1 | COMPOUND | P9 | PROTEIN | Drug1→P1→P2→P3→P4→P5→P6→P8→P9 | 14.25 | 1 |
| 003 | Drug1 | COMPOUND | DNA1 | GENE | Drug1→P1→P2→P3→P4→P5→DNA1 | 13.14 | 2 |
| 002 | Drug1 | COMPOUND | P9 | PROTEIN | Drug1→P1→P5→P6→P8→P9 | 7.89 | 3 |
| 001 | Drug1 | COMPOUND | DNA1 | GENE | Drug1→P1→P5→DNA1 | 7.22 | 4 |
| 005 | Drug1 | COMPOUND | P9 | PROTEIN | Drug1→P1→P2→P5→P6→P8→P9 | 4.83 | 5 |
| 004 | Drug1 | COMPOUND | DNA1 | GENE | Drug1→P1→P2→P5→DNA1 | 2.86 | 6 |

2100

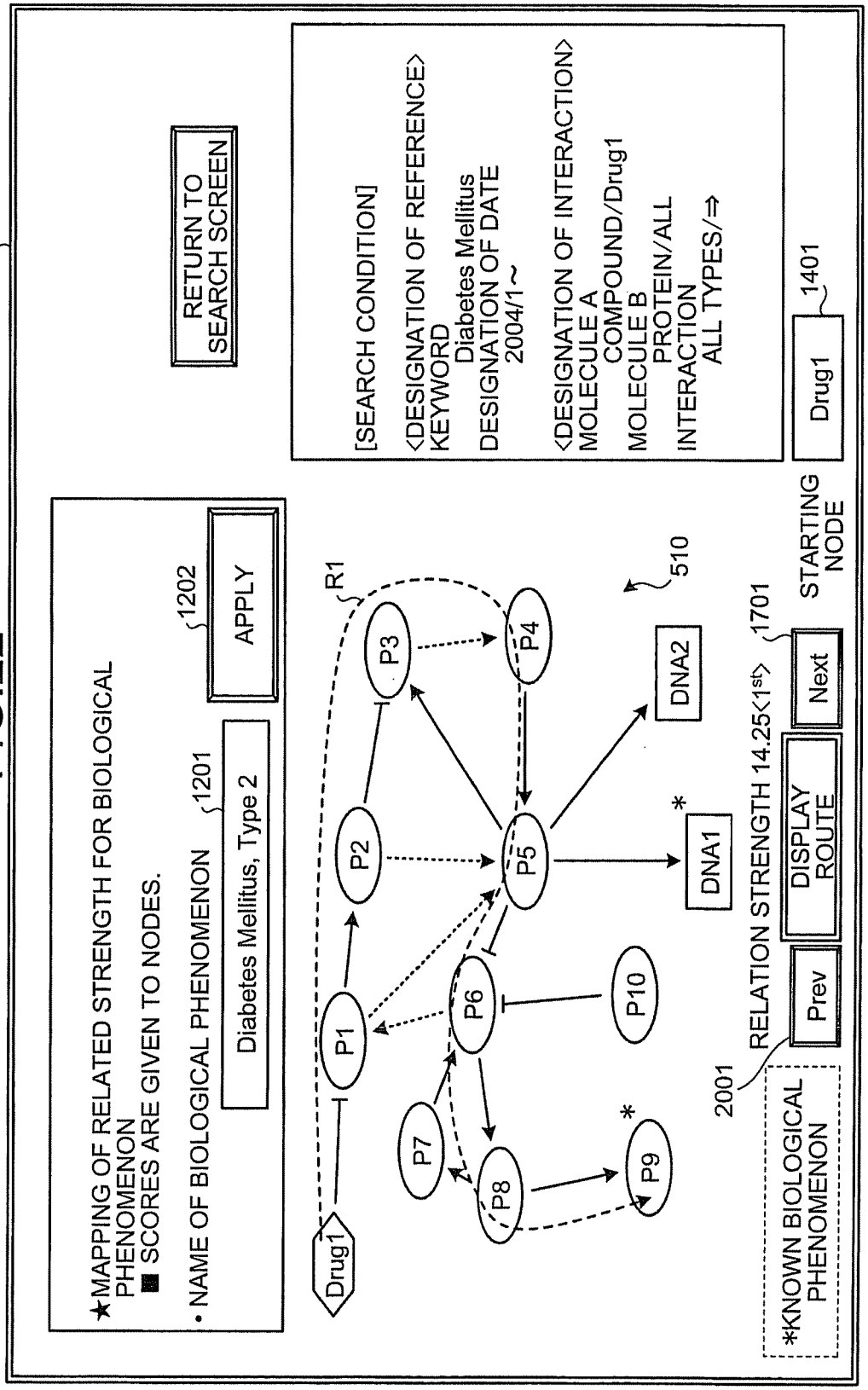

MOLECULAR NETWORK ANALYSIS SUPPORT METHOD AND APPARATUS

CROSS REFERENCE TO RELATED APPLICATION

This is a continuation application of PCT/JP2008/052149 filed on Feb. 8, 2008 which claims priority from a Japanese Patent Application No. 2007-044456 filed on Feb. 23, 2007, the contents of which are incorporated herein by reference.

FIELD

The present invention relates to molecular network analysis support technologies.

BACKGROUND

In the body of a living creature, i.e., in vivo, many chemical substances such as genes, proteins, lipids, and acids are present. These chemical substances are each present as a molecule and affect one another. The mutual influence between molecules is referred to as "molecular interaction".

Because countless molecules are present in vivo, many molecular interactions naturally occur. A molecular interaction does not occur independently and a sequence of molecular interactions often occurs. For example, "molecule A affects molecule B and as a result, molecule B forms molecule C, i.e., the molecular interactions are linked to one another like a string of beads, starting from molecule A to molecule B and, then, to the molecule C. A group of molecular interactions linked in such a manner is referred to as a "pathway".

FIG. 29 is a diagram for explaining pathways. A pathway is useful in understanding biological processes. For example, "molecule C is deformed by a molecular interaction of molecule A and molecule B and as a result, the deformation of the molecule C causes a particular disorder"; "the structure of molecule C is maintained by a molecular interaction of molecule A and molecule B and as a result, normal organ function is continued".

As described in the above examples, an overview of biological processes, regardless of normal or abnormal function, becomes understandable through pathways of molecular interaction sequences. Therefore, constructing a pathway is important in biological science related fields such as in medical services and pharmaceutical development. There are a number of pathway construction methods.

"Curation" is one method. "Curation" is a method of constructing a pathway, where a specialist called "curator" reads published literature, extracts portions that describe molecular interactions, and combines the molecular interactions to construct the pathway.

Because the curation is a method of constructing a pathway based on a human resource of curators, the amount of published literature to be read relates directly to work load. "PubMed" (see, e.g., Pubmed, on the Internet) is a website that discloses a database of published literature.

For reference, "KEGG" (see, e.g., KEGG: Kyoto Encyclopedia of Genes and Genomes, on the Internet), "BioCartal" (see, e.g., BioCarta, on the Internet), etc., are websites that disclose databases of pathways constructed by curation.

Data mining and text mining by mechanical processing are other examples of pathway construction. "Data mining" is a generic name for knowledge finding approaches involving finding hidden relations and meanings by analyzing a large amount of data using various statistical analysis approaches. In particular, obtaining specific findings and ideas by dividing text data (ordinary, natural sentences) into words, etc., and analyzing the appearance frequencies of the words and correlations therebetween is referred to as "text mining".

The methods employed for specialized text mining in biotechnology include a method of constructing a pathway, where mechanical syntax analysis is executed on "molecules" that cause molecular interaction, an "action" that each of the molecules exerts, etc. and that are included in published literature and thereby, interactions are extracted to construct a pathway. By combining the text mining and the data mining, pathways that are meaningful in terms of life sciences, e.g., "a pathway related to colon cancer" may be constructed by a computer.

"MeSH terms" (see, e.g., MeSH, on the Internet) are biological and medical terms used in biological data mining. "MeSH" stands for Medical Subject Headings and refers to a group of biological and medical terms. MeSH are already given to published literature and by calculating the total amount of the MeSH terms, it becomes possible to analyze the significance a particular group of published literature has biologically and medically.

Further, website disclose a database formed by correlating biological and medical significance to molecules constituting each pathway. OMIM (see, e.g., OMIM, on the Internet) and H-invDB (see, e.g., H-inv DB, on the Internet) each correspond to such a website. Both databases are formed by correlating genetic significance to the molecules. The biological and medical significance of a molecule, a gene, etc. may be identified by using the data in each of these databases in data mining.

BMC Bioinformatics 2005, 6 Suppl 1 S4. Epub 2005 May 24 is a reference concerning text mining specialized for biology and medicine. "BioCreAtIvE" (see, e.g., BioCreAtIvE, on the Internet) is a research organization. Websites that disclose a database having interaction information preliminarily stored therein include "HPRD" (see, e.g., Human Protein Reference Database, on the Internet) and "BIND" (see, e.g., BIND, on the Internet). These websites have registered therein direct interactions between proteins such as "bonding". Information on the molecular interactions registered therein may be collectively obtained and may be used for data mining, etc.

"ResNet" from Ariadne Genomics, Inc., is a commercial database formed by correlating "types" and "functions" of molecules as the significance of a molecular interaction and the molecules that cause the molecular interaction. Such a database may be purchased and data mining may be executed using the database.

"MedTAK", from Celestare Lexico-Sciences, Inc., is software that has added functions of text mining and data mining. This software analyzes the appearance frequencies, etc., of "a group of molecules", "MeSH terms", etc., described in a group of published literature and thereby, supports the extraction of biological and medical meanings thereof. However, the text mining technique of the software has no function of extracting molecular interactions.

When a molecular network is constructed using a pathway, "a method of selecting a route that has biological and medical significance" is necessary. Due to this point of finding "biological and medical significance", the circumstances of the selection of a route for the pathway is different from that of ordinary route selection in a network. There are a number of route selecting approaches for a pathway.

For example, Japanese Laid-Open Patent Publication No. 2006-146380 introduces a conventional technique of giving "biological and medical" information concerning, for example, a disorder, to a molecular interaction. However, as to selection of a route between molecules, the shortest route is always selected according to this approach.

International Publication Pamphlet No. WO2003-077159 introduces a method of using a set of routes among two or more molecules called "subnet" as an approach of selecting a route that is selected taking into account the degree of relation to a disorder. Subnets each concern a disorder, etc., and are constructed in advance. When a route is sought, if a subnet concerning a disorder is hit, the selection of a route related to the disorder is enabled.

Japanese Laid-Open Patent Publication No. 2005-122231 discloses a method of displaying a screen to construct a network of terms such as compounds concerning a gene, names of disorders, and proteins. This method is an approach where a user designates a term group 1 and a term group 2 to depict, as a network, information from published literature that suggest relations among the terms.

However, due to shape characteristics of the network, a problem arises for a pathway in terms of "route selection", i.e., because the number of references registered in "PubMed" is tremendous, the number of molecular interactions extracted is also tremendous. Because the number of molecular interactions, which are components of a pathway, is tremendous, a problem arises in that the shape of the pathway naturally forms a more extensive and complicated network and the selection of a route becomes difficult. An extensive network for which selection of a route is difficult is depicted in FIG. 30.

A pathway may be constructed by reducing the number of molecular interactions using curation. However, as of November 2006, the number of references in "PubMed" was at least 16 million and this number increases by 50 to 60 thousand per month. Therefore, a problem arises in that the number of references to be read is tremendous even at present and therefore, construction consumes a tremendous amount of time.

The number of published literature continues to increase and therefore, a problem arises in that "responses to new theories", etc., using information for updating is limited. Hence, a problem has arisen in curation whereby a biased pathway may be constructed based on subjectivity on the part of the curator.

In Japanese Laid-Open Patent Publication No. 2006-146380, when multiple routes are present that each have a long route length and multiple biological and medical meanings, examination is impossible and the technique is insufficient for clarification of the mechanism of a disorder, etc. Multiple routes often occur on a pathway and no correlation between the shortness of the route length and the biological and medical meanings has been confirmed.

Research on the mechanism of an in vivo molecule is ongoing and therefore, omissions concerning new biological and medical information occur in a subnet constructed in advance. However, in International Publication Pamphlet No. WO2003-077159, no alternative means is presented. International Publication Pamphlet No. WO2003-077159 includes no description on any approach of using a computer, etc. to construct a subnet that is related to disorders and that may be updated continuously. Therefore, the approach therein is insufficient.

In Japanese Laid-Open Patent Publication No. 2005-122231, no approach is presented of displaying, with respect to each molecule and each sequence of molecules, the relation with the biological and medical meanings that indicate a specific disorder. Therefore, the method described in Japanese Laid-Open Patent Publication No. 2005-122231 is insufficient. Databases that give medical and biological meanings to each of the genes stored therein such as OMIM and H-invDB, and HPRD, BIND, etc. that have information on interactions stored therein are effective as materials for data mining, but themselves have no function of pathway construction. Therefore, examination of a biological phenomenon by way of a pathway is not possible and naturally, these databases do not contribute to the selection of a route.

MedTAK software from Celestare Lexico-Sciences, Inc., extracts medical and biological meanings from a group of published literature using a data mining technique. However, MedTAK extracts no molecular interaction. Therefore, the software is unable to construct a pathway and does not contribute to the selection of a route therefor.

Hence, a problem arises in that for Japanese Laid-Open Patent Publication Nos. 2005-122231 and 2006-146380 as well as International Publication Pamphlet No. WO2003-077159, the databases (OMIM, H-invDB, HPRD, and BIND), and the software (MedTAK) are insufficient in terms of "a method for selecting a route that has biological and medical meanings" for a pathway.

SUMMARY

According to an aspect of an embodiment, a molecular network analysis support method includes receiving designation of a biological phenomenon, extracting an interaction from a molecular network, and calculating a relation strength between the designated biological phenomenon and the extracted interaction.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 2 is a diagram for explaining storage content of a medical reference DB used by a molecular network analysis support apparatus 100 according to the present embodiment;

FIG. 3 is a diagram for explaining storage content of an interaction DB used by the molecular network analysis support apparatus 100 according to the present embodiment;

FIG. 4 is a diagram for explaining the storage content of the pharmacology DB used by the molecular network analysis support apparatus 100 according to the present embodiment;

FIG. 12 is a diagram for explaining a display screen of a molecular network 510;

FIG. 13 is a diagram for explaining a relation strength S1 between an interaction (non-redundant interaction) and a designated biological phenomenon for each molecule pair;

FIG. 14 is a diagram for explaining a mapping screen of the relation strength S1;

FIG. 17 is a diagram for explaining a mapping screen 1400 after receipt of selection of the molecule that is the starting node;

FIG. 18 is a diagram for explaining a retrieval result 1110 by a retrieving unit 1106;

FIG. 19 is a diagram for explaining the mapping screen 1400 that displays the retrieved routes (Part I);

FIG. 20 is another diagram for explaining the mapping screen 1400 that displays the retrieved routes (Part II);

FIG. 21 is a diagram for explaining a sorted result 2100 obtained by sorting the retrieval result 1110 by the retrieving unit 1106;

FIG. 22 is another diagram for explaining the mapping screen 1400 that displays the retrieved routes (Part III);

DESCRIPTION OF EMBODIMENTS

Preferred embodiments of the present invention will be explained with reference to the accompanying drawings.

Herein, "molecules" that interact include genes, proteins, and compounds in addition to molecules constituting a chemical substance that is present in vivo.

Figure 1:
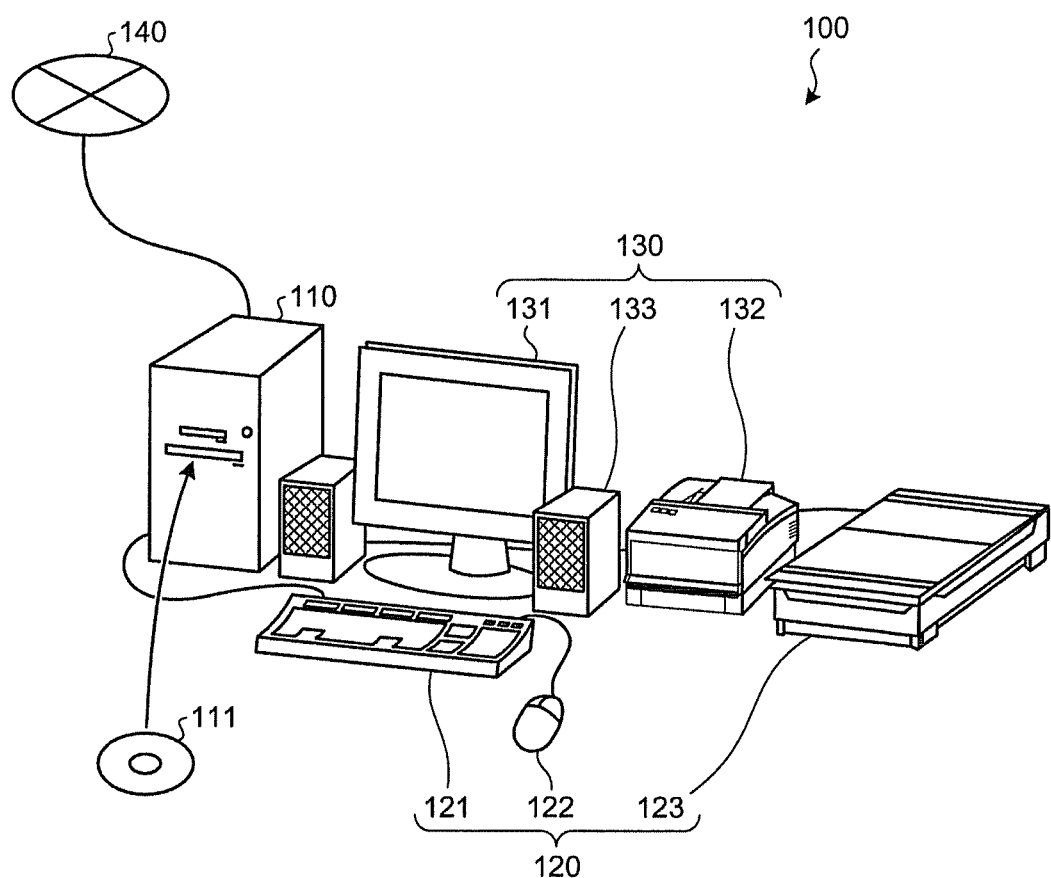
FIG. 1 is a block diagram of a molecular network analysis support apparatus according to an embodiment of the present invention.

FIG. 1 is a block diagram of a molecular network analysis support apparatus according to an embodiment of the present invention.

As depicted in FIG. 1, a molecular network analysis support apparatus 100 includes a computer 110, an input device 120, and an output device 130, and may be connected with a network 140, e.g., a local area network (LAN), a wide area network (WAN), or the Internet through a non-depicted router or a modem.

The computer 110 has a central processing unit (CPU), a memory, and an interface. The CPU governs overall control of the molecular network analysis support apparatus 100. The memory is formed of, for example, read-only memory (ROM), a random access memory (RAM), a hard disk (HD), an optical disk 111, or a flash memory. The memory is used as a work area of the CPU.

Various programs are stored in the memory and loaded in response to a command from the CPU. The reading and the writing of data with respect to the HD and the optical disk 111 are controlled by a disk drive. The optical disk 111 and the flash memory are removable. The interface controls input from the input device 120, output to the output device 130, and transmission/reception with respect to the network 140.

As the input device 120, a keyboard 121, a mouse 122, and a scanner 123 are adopted. The keyboard 121 includes keys to input, for example, characters, numeric figures, and various kinds of instructions, and data is input through the keyboard 121. The keyboard 121 may be a touch panel. The mouse 122 is used to move a cursor, select a range, move a window, or change window size. The scanner 123 optically reads an image as image data, which is stored in the memory of the computer 110. The scanner 123 may have an optical character recognition (OCR) function.

As the output device 130, a display 131, a printer 132, a speaker 133, etc. are adopted. The display 131 displays a cursor, an icon, or a tool box as well as data, such as text, an image, and function information. The printer 132 prints image data or text data. The speaker 132 outputs sound, e.g., a sound effect or a text-to-voice converted sound.

The storage content of a medical reference database (DB) used by the molecular network analysis support apparatus 100 according to the present embodiment will be described. FIG. 2 is a diagram for explaining the storage content of the medical reference DB used by the molecular network analysis support apparatus 100 according to the present embodiment.

As depicted in FIG. 2, a medical reference DB 200 is a database that is open to the public and for each reference ID identifying a medical reference, stores therein the title, the abstract (summary), the author(s), the date of publication, and the MeSH terms of the medical reference. "MeSH terms" are biological and medical terms that are used for searching a reference. The biological and medical meanings that a specific group of medical references have may be analyzed by calculating statistical amounts of MeSH terms given to the medical references.

A function of the medical reference DB 200 is implemented by a recording medium such as an HD or a semiconductor memory. The medical reference DB 200 may be incorporated in the molecular network analysis support apparatus 100 or may be accessible to the molecular network analysis support apparatus 100 from an external server through the network 140.

The storage content of an interaction DB used by the molecular network analysis support apparatus 100 according to the present embodiment will be described. FIG. 3 is a diagram for explaining the storage content of the interaction DB used by the molecular network analysis support apparatus 100 according to the present embodiment.

As depicted in FIG. 3, the interaction DB 300 identifies a molecular interaction (hereinafter, simply "interaction") for each record by storing therein the standard molecular notation of a molecule "A" and its molecule type; the standard molecular notation of a molecule "B" and its molecule type; the reference ID; the type of interaction; and the direction of the interaction.

The "molecule A" is a molecule that constitutes an interaction and that is on one end, and the "molecule B" is a molecule on the other end. The "standard molecular notation"

is the standard notation of a molecule that constitutes an interaction. The "molecule type" indicates the kind of molecule that constitutes an interaction (such as protein or compound).

A "reference ID" is the ID of a medical reference that describes therein a molecule identifying an interaction, and the reference ID correlates the medical reference with the medical reference DB 200. An "interaction type" represents the type (such as inhibition, bonding, or activation) of interaction between molecules (the molecule A and the molecule B). The "direction of an interaction" is information that identifies whether a molecule that identifies an interaction is affected by another molecule or affects another molecule. For example, when the direction is indicated as "→", "→" indicates that the molecule A affects the molecule B in an interaction.

An interaction is identified for each record by the standard molecular notation of the molecule "A" and its molecule type; the standard molecular notation of the molecule "B" and its molecule type; the reference ID; the type of interaction; and the direction of the interaction. An interaction is constructed using information extracted by curation, or a syntax analysis by natural language processing (for example, MeSH, on the Internet).

A function of the interaction DB 300 is implemented by a recording medium such as an HD or a semiconductor memory. The interaction DB 300 may be incorporated in the molecular network analysis support apparatus 100 or may be accessible to the molecular network analysis support apparatus 100 from an external server through the network 140.

The storage content of a pharmacology DB used by the molecular network analysis support apparatus 100 according to the present embodiment will be described. FIG. 4 is a diagram for explaining the storage content of the pharmacology DB used by the molecular network analysis support apparatus 100 according to the present embodiment.

The pharmacology DB 400 depicted in FIG. 4 is a database that stores therein information concerning the results of an experiment indicating that mutation of a specific protein, knocking out, knocking down, or overexpression relates to a disorder, as indicated in examples 1 and 2 below.

EXAMPLE 1

Overexpression of Gene "X" due to Diabetes Mellitus Type 2

EXAMPLE 2

Liver Cirrhosis induced when a Gene "Y" is Knocked down in an RNAi Experiment

The pharmacology DB 400 stores therein database IDs, the standard molecular notation of a protein of interest, names of related in vivo phenomena, and related descriptions thereof. A "database ID" is an ID that identifies a database that is curated. "Related description" is text data describing therein the type of experiment and a disorder with which relation is determined. New pharmacological information discovered through the molecular network analysis support apparatus 100 and information discovered experimentally, etc., may also be additionally registered. Thereby, the comprehensiveness of the pharmacology DB 400 may be improved.

A function of the pharmacology DB 400 is implemented by a recording medium such as an HD or a semiconductor memory. The pharmacology DB 400 may be incorporated in the molecular network analysis support apparatus 100 or may be accessible to the molecular network analysis support apparatus 100 from an external server through the network 140.

Figure 5:
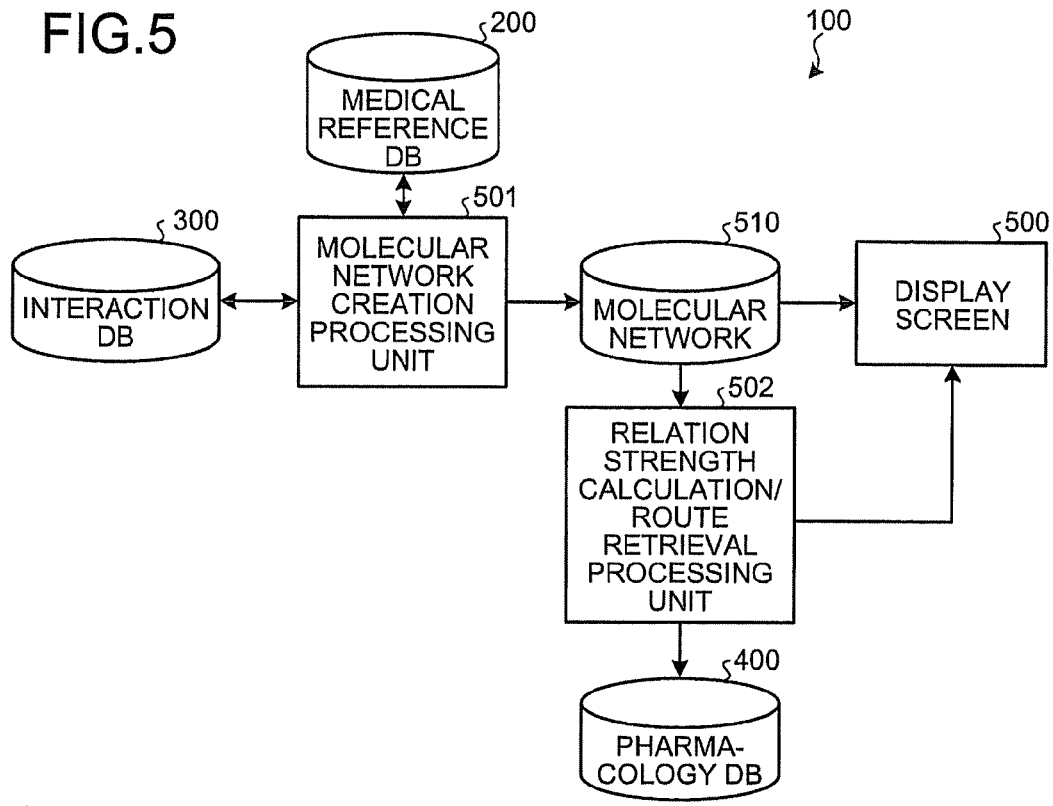
FIG. 5 is a block diagram of a functional configuration of the molecular network analysis support apparatus 100 according to the present embodiment.

A functional configuration of the molecular network analysis support apparatus 100 according to the present embodiment n will be described. FIG. 5 is a block diagram of a functional configuration of the molecular network analysis support apparatus 100 according to the present embodiment. As depicted in FIG. 5, the molecular network analysis support apparatus 100 includes a molecular network creation processing unit 501 and a relation strength calculation/route retrieval processing unit 502. Respective functions of the molecular network creation processing unit 501 and the relation strength calculation/route retrieval processing unit 502 may be implemented by causing the CPU to execute a program concerning the function stored in a memory or by an input and output I/F.

Data output from the molecular network creation processing unit 501 and the relation strength calculation/route retrieval processing unit 502 is retained in a memory. Functions of units at connection destinations indicated by arrows in FIG. 5 are implemented by the data output from the function that is the connection origin being read from the memory and the CPU being caused to execute a program concerning the function.

The molecular network creation processing unit 501 has a function of creating, by referring to the medical reference DB 200 and the interaction DB 300, a molecular network 510 that a user desires to analyze from pathways. The molecular network 510 created is displayed on a display screen 500. Details concerning the molecular network creation processing unit 501 will be described with reference to FIG. 6.

The relation strength calculation/route retrieval processing unit 502 calculates the relation strength of each interaction of the molecular network 510 by referring to the pharmacology DB 400, and retrieves a route that has biological meaning from among a tremendous number of routes in the molecular network 510. The relation strength calculation/route retrieval processing unit 502 may further calculate the relation strength of a retrieved route.

The calculated relation strength is displayed on the display screen 500, by indicating the corresponding interaction in the molecular network 510 in a color according to its relation strength or by depicting a value in the vicinity of the interaction. A line drawn representing a retrieved route is also displayed on the display screen 500 such that the line is located along the interaction in the molecular network 510. Details concerning the relation strength calculation/route retrieval processing unit 502 will be described with reference to FIG. 11.

Figure 6:
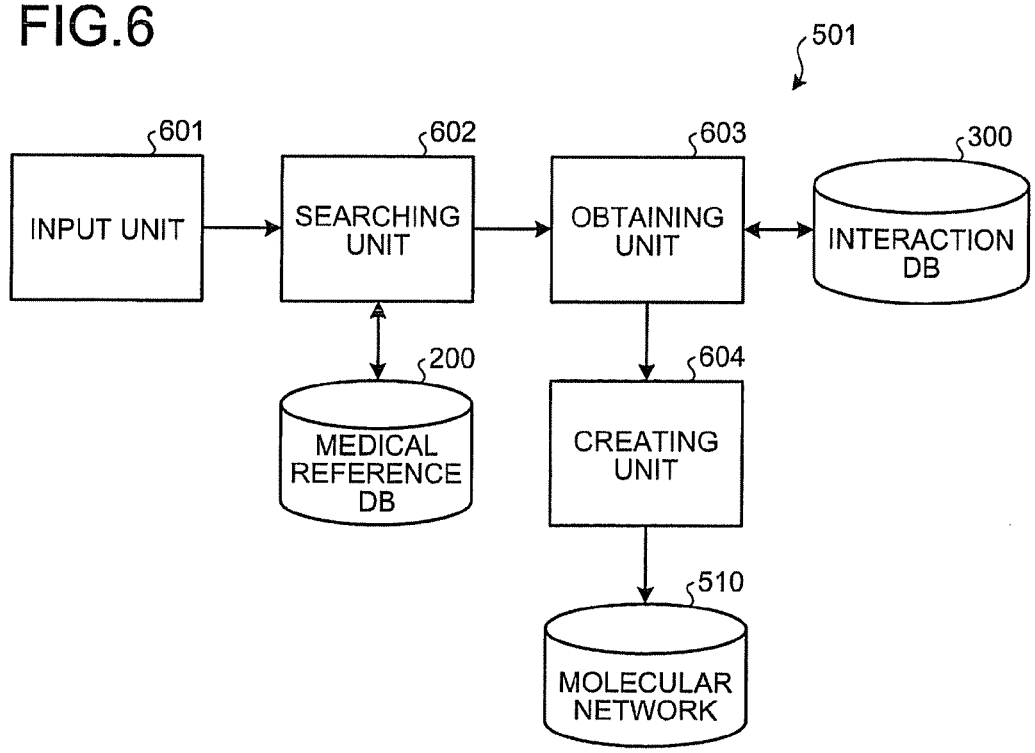
FIG. 6 is a block diagram of a functional configuration of a molecular network creation processing unit 501 depicted in FIG. 5.

FIG. 6 is a block diagram of a functional configuration of the molecular network creation processing unit 501 depicted in FIG. 5. As depicted in FIG. 6, the molecular network creation processing unit 501 includes an input unit 601, a searching unit 602, an obtaining unit 603, and a creating unit 604.

The input unit 601 has a function of receiving input of a search condition concerning a molecule or an interaction. The "search condition concerning a molecule or an interaction" is information identifying a molecule or an interaction that is included in the molecular network 510 and that a user desires to analyze. The condition may be, for example, the standard molecular notation of a molecule "A" and its molecule type; the standard molecular notation of a molecule "B" and its molecule type; the reference ID; the type of interaction; and the direction of the interaction, depicted in FIG. 3. Further, a free keyword such as a MeSH term may be input as the search condition.

Figure 7A:
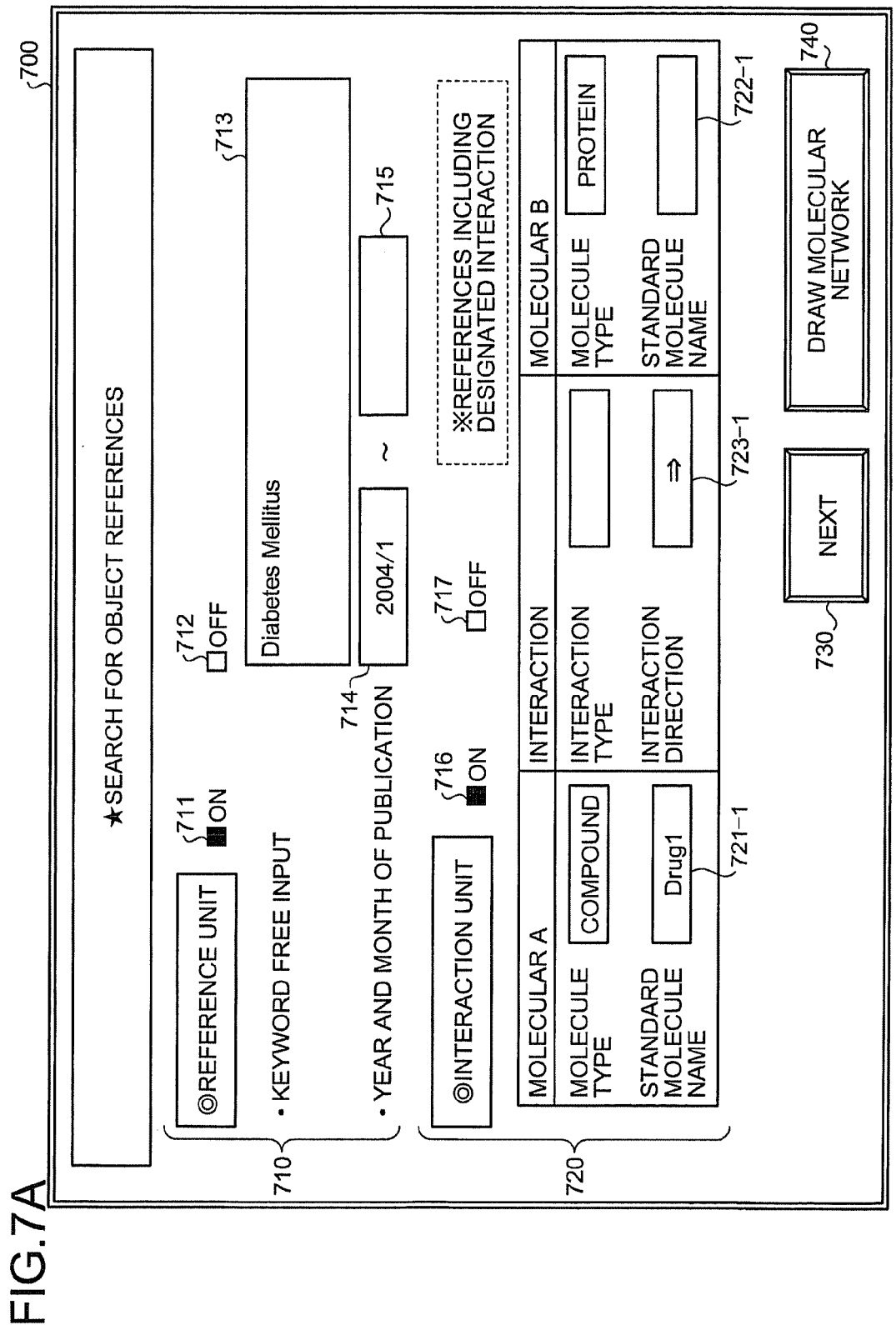
FIG. 7A is a diagram for explaining a search screen of a search condition.

Exemplary input of a search condition will be described. FIG. 7A is a diagram for explaining a search screen of a search condition. As depicted in FIG. 7A, a reference unit area 710 into which a search condition is input for each reference and an interaction unit area 720 into which a search condition is input for each interaction that a user desires to analyze are displayed on the search screen 700.

When a search is to be executed by reference using a search condition, a box 711 is checked that represents "ON" in the reference unit area 710. When a search is not to be executed by reference using a search condition, a box 712 is checked that represents "OFF". In the example depicted in FIG. 7, the box 711 is checked.

The user freely inputs keywords in a keyword input column 713. In the example depicted in FIG. 7, "Diabetes Mellitus" is input as keywords. The medical references to be searched may be more strictly selected by an input of the year and the month of publication into year and month of publication input columns 714 and 715.

When a search is to be executed by interaction using a search condition, a box 716 is checked that represents "ON" in the interaction unit area 720. When a search is not to be executed by interaction using a search condition, a box 717 is checked that represents "OFF". In FIG. 7, the box 716 is checked; thus, in the example depicted in FIG. 7, the search is to be executed by reference and by interaction.

To an input area 721-1 for the molecule A, the molecule type and the standard molecular notation of the molecule A may be input as search conditions. To an input area 722-1 for the molecule B, the molecule type and the standard molecular notation of the molecule B may be input as search conditions. To an input area 723-1, the type of interaction and the direction of the interaction may be input as search conditions. When a designation button 730 is clicked, a search condition for the interaction may be newly input.

Figure 7B:
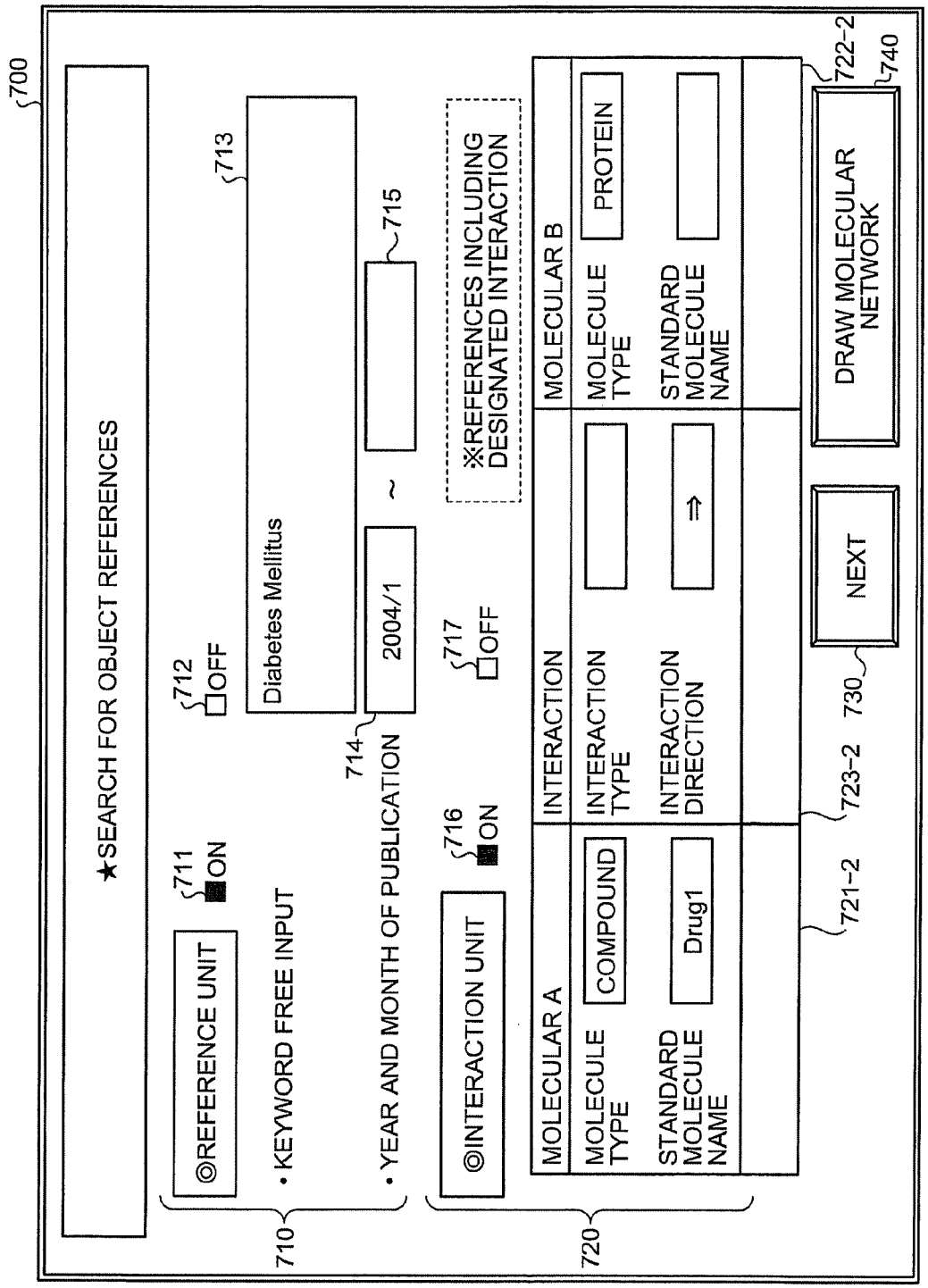
FIG. 7B is a diagram for explaining a search screen 700 after the clicking of a designation button 730.

FIG. 7B is a diagram for explaining the search screen 700 after the clicking of the designation button 730. As depicted in FIG. 7B, new input areas 721-2, 722-2, and 723-2 appear. As described, each time the designation button 730 is clicked, input areas {721-1, 722-1, 723-1}, {721-2, 722-2, 723-2}, . . . appear and new search conditions may be input.

When a drawing button 740 is clicked after the search conditions have been input, a medical reference searching process, an interaction identification information obtaining process, and a molecular-network-510 creating process are executed. The molecular network 510 created is displayed on the display screen 500.

The searching unit 602 depicted in FIG. 6 has a function of searching in the medical reference DB 200 for medical references that coincide with or relate to the search conditions input by the input unit 601. More specifically, for example, when a check is input into the box 711 of the reference unit area 710 depicted in FIGS. 7A and 7B, the searching unit 602 searches in the medical reference DB 200 for medical references that coincide with or relate to the search conditions input into the reference unit area 710. The search result is a set of reference IDs of the medical references.

Yet more specifically, the searching unit 602 searches for medical references having keywords that coincide with the keywords input into the keyword input column 713 (input keywords) and medical references partially coinciding with the input keywords. When a period for the year and the month of publication is designated using the input columns 714 and 715, the searching unit 602 may restrict medical references to those published during the period designated.

When a check is input in the box 716 of the interaction unit area 720 depicted in FIGS. 7A and 7B, the searching unit 602 searches in the medical reference DB 200 for medical references that coincide with or relate to the search conditions input into the interaction unit area 720. More specifically, when the molecule A is designated using the input area 721-1, the reference IDs of medical references each describing therein the molecule type or the standard molecule name of the molecule A are searched for.

When the molecule B is designated using the input area 722-1, medical references each describing therein the molecule type or the standard molecule name of the molecule B are searched for. When an interaction is designated using the input area 723-1, the reference IDs of medical references each describing therein the type and the direction of the interaction are searched for.

In the example depicted in FIG. 7A, the reference IDs of medical references are searched for that describe therein an interaction between the molecules A and B, where the molecule type and the standard molecule name of the molecule A is "compound" and "Drug1", the molecule type of the molecule B is "protein", and interaction direction is "→" (where the molecule A is on the left of "→" and the molecule B is on the right of "→").

The MeSH terms of the medical reference DB 200 are have a hierarchical structure and therefore, the MeSH terms may also be searched for including the MeSH terms in lower hierarchical layers. More specifically, for example, an MeSH term, "Diabetes Mellitus, Type 2" (non-insulin-dependent diabetes mellitus) is present. However, "Diabetes Mellitus, Lipoatrophic" is present in a different layer and therefore, more extensive interactions may be extracted by concurrently searching for medical references each having this attribute.

The obtaining unit 603 depicted in FIG. 6 has a function of obtaining a set of interactions correlated with the medical references that are retrieved by the searching unit 602 from the interaction DB 300. More specifically, for example, using the retrieved reference IDs of the medical references as keys, the obtaining unit 603 extracts, from the interaction DB 300 and as the interaction, records having the reference IDs.

Figure 8:
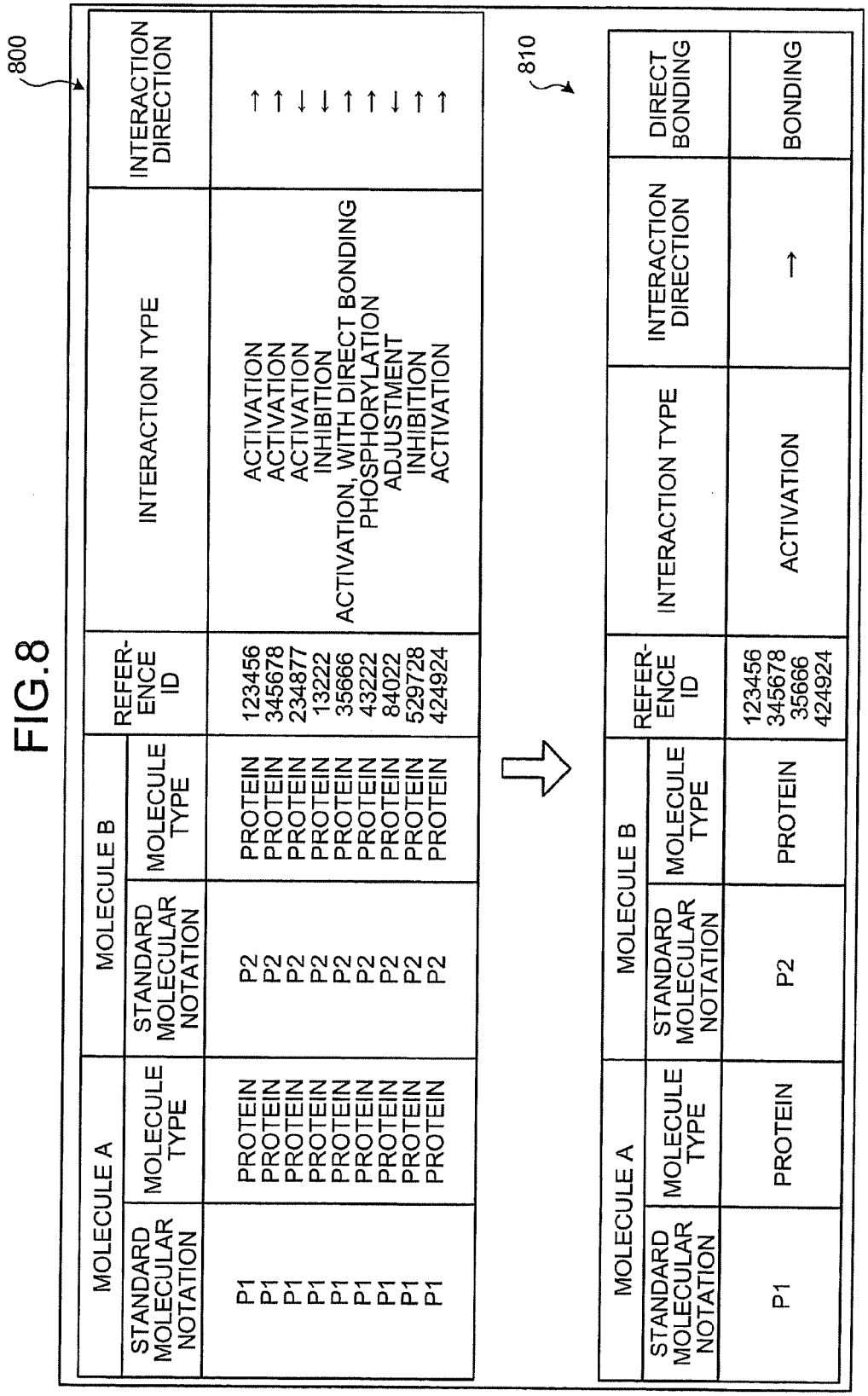
FIG. 8 is a diagram for explaining a set of interactions obtained by an obtaining unit 603.

FIG. 8 is a diagram for explaining the set of interactions obtained by the obtaining unit 603. All the interactions identified from the medical references having the retrieved reference IDs are covered by a set 800 of interactions. However, in this example, for simplicity, only the result obtained when a protein P1 is the molecule A and a protein P2 is the molecule B is depicted.

The creating unit 604 depicted in FIG. 6 has a function of creating the molecular network 510 according to the search conditions by linking molecule pairs identified by the set 800 of interactions obtained by the obtaining unit 603. More specifically, for example, even when the combination of the molecules A and B is same, the interaction type and the direction of the interaction differ according to medical reference and therefore, the set 800 of interactions obtained by the obtaining unit 603 is consolidated.

The method of consolidation will be described using the set 800 of interactions depicted in FIG. 8. A numeral 810 denotes the consolidation result of the set 800 of interactions. The consolidation result 810 is referred to as "non-redundant interaction". The set 800 of interactions is a set of interactions concerning the molecule A that is the protein P1 and the molecule B that is the protein P2.

For this combination of the molecule A and the molecule B, a decision based on largest quantity is made with respect to the number of reference IDs for each of the combinations of the interaction types and the interaction directions, and the combination with the largest number of reference IDs is determined as the non-redundant interaction between the molecules A and B. In the example depicted in FIG. 8, the number of reference IDs for the interaction type "activation" and the interaction direction "→" is the largest (=four).

The consolidation process depicted in FIG. 8 is executed for each molecule pair (the molecules A and B) that identifies the interaction, and non-redundant interactions are linked using the molecule that is common to the interactions. Thereby, the molecular network 510 is created.

Figure 9:
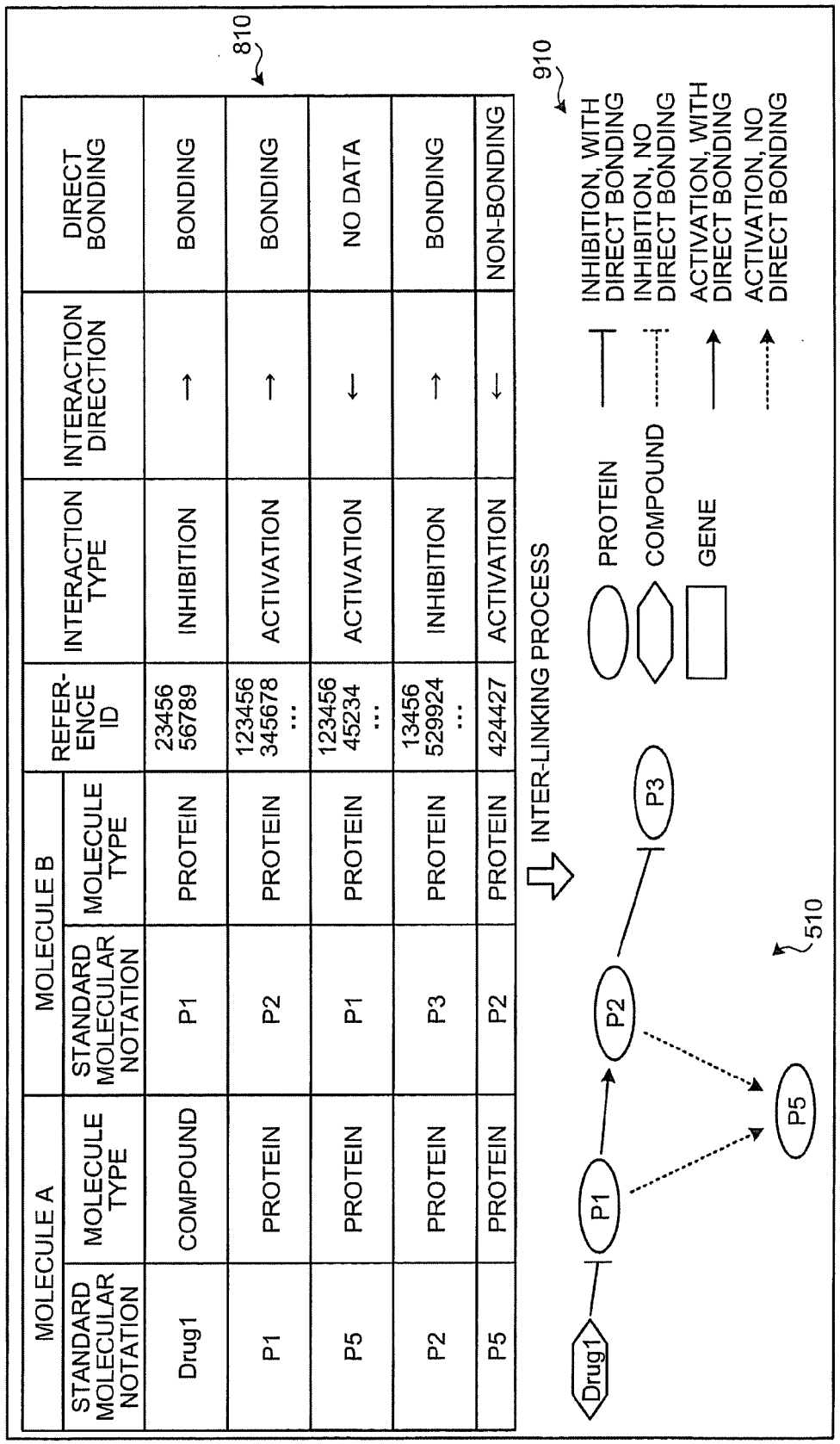
FIG. 9 is a diagram for explaining a set 810 of non-redundant interactions and a linking result.

FIG. 9 is a diagram for explaining a set 810 of non-redundant interactions and a linking result. As depicted in FIG. 9, the linking result 910 becomes the molecular network 510. In the molecular network 510, a molecule type is represented by a figure; a standard molecular notation is represented by a character string within the figure; the direction of interaction is indicated by an arrow; and the interaction type is indicated by the type of the arrow.

The molecular network 510 is not only a simple directed graph but is also a directed graph whose nodes themselves each incorporate therein the type (such as protein, compound, or DNA), the attribute of the interaction (such as activation, inhibition, or transcription activation), and information as to whether the direct bonding has been confirmed experimentally.

Figure 10:
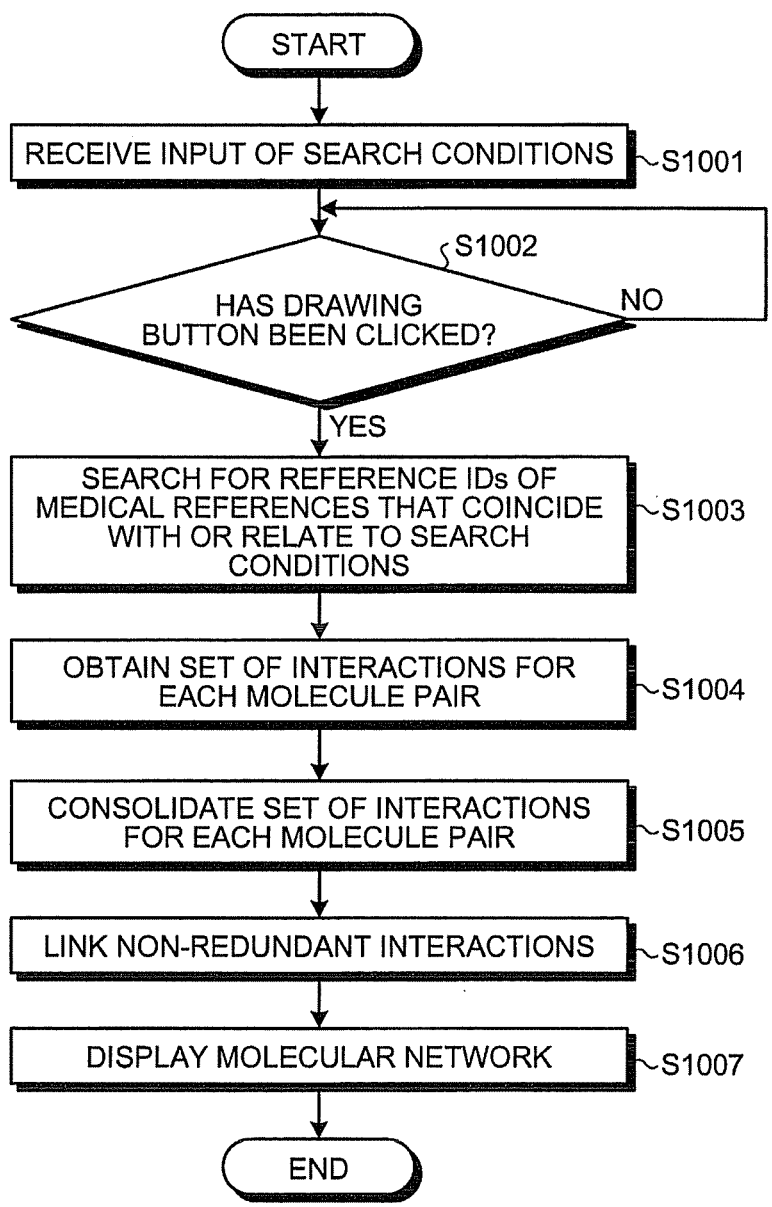
FIG. 10 is a flowchart of a molecular network creating process performed by the molecular network analysis support apparatus 100 according to the present embodiment.

FIG. 10 is a flowchart of the molecular network creating process performed by the molecular network analysis support apparatus 100 according to the present embodiment.

As depicted in FIG. 10, the input unit 601 receives input of search conditions (step S1001). More specifically, for example, various types of search conditions are input by the user operation into the search screen 700 depicted in FIGS. 7A and 7B. Waiting occurs until detection of a clicking of the drawing button 740 (step S1002: NO).

When the clicking of the drawing button 740 has been detected (step S1002: YES), the searching unit 602 searches for reference IDs of medical references that coincide with or relate to the search conditions (step S1003). The obtaining unit 603 obtains a set of interactions for each molecule pair from the interaction DB 300 (step S1004).

The creating unit 604 consolidates the set of interactions for each molecule pair (step S1005). Thereby, non-redundant interactions for each molecule pair may be obtained. The non-redundant interactions are linked using molecules that are common in the interactions (step S1006). Thereby, the molecular network 510 may be created. Thereafter, the molecular network 510 is displayed on the display screen 500 (step S1007).

In this manner, the above creating unit 604 may extract only a molecular network 510 that the user desires to analyze from a pathway including a tremendous number of interactions strung together like beads.

Figure 11:
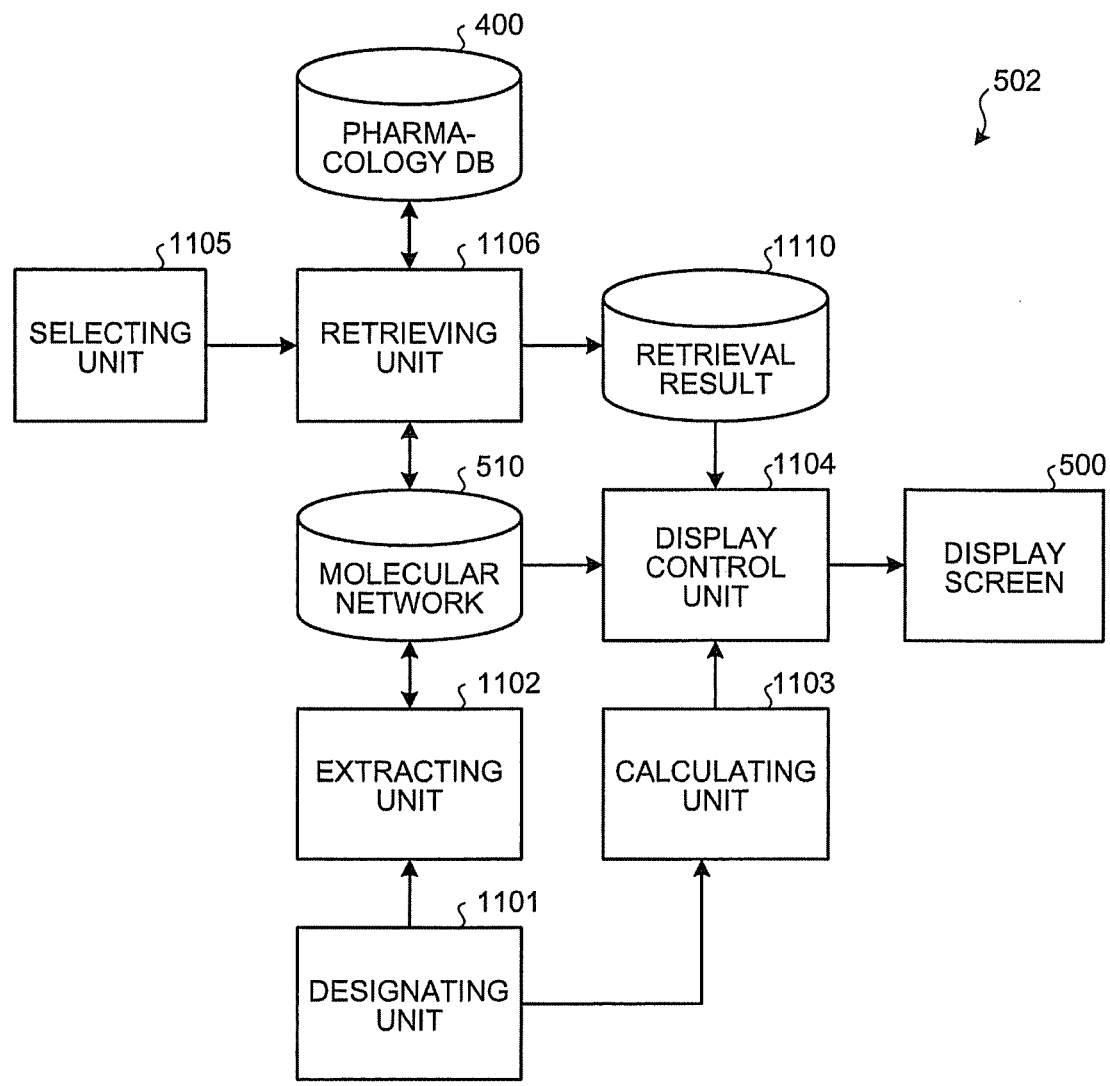
FIG. 11 is a block diagram of a functional configuration of a relation strength calculation/route retrieval processing unit 502 depicted in FIG. 5.

FIG. 11 is a block diagram of a functional configuration of the relation strength calculation/route retrieval processing unit 502 depicted in FIG. 5. As depicted in FIG. 11, the relation strength calculation/route retrieval processing unit 502 includes a designating unit 1101, an extracting unit 1102, a calculating unit 1103, a display control unit 1104, a selecting unit 1105, and a retrieving unit 1106.

The designating unit 1101 has a function of receiving designation of an arbitrary biological phenomenon. A biological phenomenon is a phenomenon that occurs in vivo such as a disorder or a disease. More specifically, for example, through a user input of a MeSH term that is the name of a biological phenomenon, designation of the biological phenomenon is received. Such a biological phenomenon is referred to as "designated biological phenomenon".

FIG. 12 is a diagram for explaining a display screen of the molecular network 510. A display screen 1200 depicted in FIG. 12 is a screen that is displayed by clicking the drawing button 740 depicted in FIG. 7A or 7B. An input column 1201 is an input column to which the name of a biological phenomenon is input. In this example, "Diabetes Mellitus, Type 2" (non-insulin-dependent diabetes mellitus) is input. Designation of the biological phenomenon is received by a clicking of an "apply" button 1202.

When a biological phenomenon is designated, the extracting unit 1102 depicted in FIG. 11 has a function of extracting an arbitrary interaction from the molecular network 510. The molecular network 510 is a network formed by linking non-redundant interactions and therefore, the interaction extracted is a non-redundant interaction. More specifically, for example, a non-redundant interaction is extracted from the set of non-redundant interactions 810 depicted in FIG. 9.

The calculating unit 1103 has a function of calculating the relation strength between a designated biological phenomenon and an interaction (non-redundant interaction) extracted by the extracting unit 1102. The "relation strength" between a biological phenomenon and an interaction is information that indicates the strength of the connection between the biological phenomenon and the interaction. When this information is expressed by a value, the relation strength becomes stronger as the value becomes larger. A molecule pair that identifies an interaction and whose relation strength is to be calculated is referred to as "molecule pair of interest".

This relation strength S1 may be calculated, for example, according to the scores of Equations (1) to (3).

$$S1 = \text{Log}(X/Y) \tag{1}$$

$$X = X2/X1 \tag{2}$$

$$Y = Y2/Y1 \tag{3}$$

"X1" is the number of references in a set of medical references in which a molecule pair of interest appears, among all the medical references in MEDLINE. "X2" is the number of references in a set of medical references in which an interaction identified by the molecule pair of interest appears, among the medical references in which a designated biological phenomenon (MeSH term) appears.

"Y1" is the number of references in a set of medical references in which interactions identified by all the molecule pairs extracted from all the medical references in MEDLINE appear. "Y2" is the number of references in a set of medical references in which the interactions identified by all the molecule pairs appear, among a set of medical references in which the designated biological phenomenon (MeSH term) appears.

FIG. 13 is a diagram for explaining the relation strength S1 between an interaction (non-redundant interaction) and a designated biological phenomenon for each molecule pair. As depicted in FIG. 13, each corresponding color is determined according to the magnitude of the relation strength S1. The corresponding color is coloring applied to an edge (arrow) that represents an interaction of the molecular network 510.

The calculating unit 1103 may calculate the relation strength S1 by limiting the conditions such as the same interaction type, presence or absence of directivity, and the same molecule pair type. The calculating unit 1103 may further calculate the relation strength S1 by utilizing the structure of MeSH terms. Thereby, a molecule pair that is specific to a designated biological phenomenon may be estimated and this may help to understand the mechanism of a disorder. The relation strength S1 is calculated not as a binary value but as one of consecutive values and therefore, the interaction to be noted may be grasped stepwise by sorting the group of interactions using the relation strength S1 as a key.

FIG. 14 is a diagram for explaining a mapping screen of the relation strength S1. The mapping screen 1400 is displayed by clicking the application button 1202 depicted in FIG. 12.

The calculating unit 1103 also calculates relation strength S2 between a designated biological phenomenon and each of the molecules of a molecule pair of interest that identifies an interaction. The relation strength S2 may be calculated, for example, according to the scores of Equations (3) to (5).

$$S2 = \text{Log}(x/Y) \tag{4}$$

$$x = x2/x1 \tag{5}$$

"x1" is the number of references in a set of medical references in which a molecule of the object pair appears, among all the medical references in MEDLINE. "x2" is the number of references in a set of medical references in which an interaction identified by a molecule of the molecule pair of interest appears, among the medical references in which a designated biological phenomenon (MeSH term) appears.

Figures 15, 16:
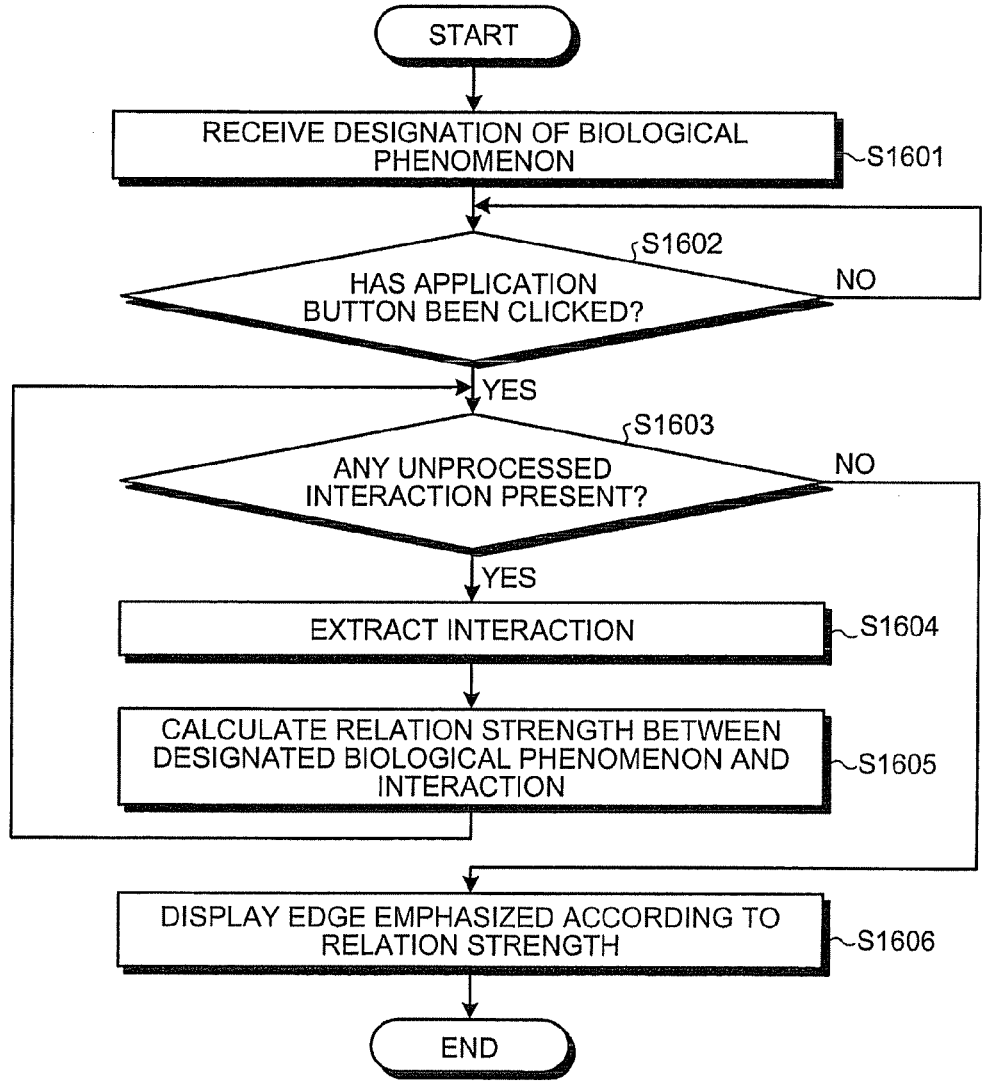
FIG. 15 is a diagram for explaining the relation strength S2 between a molecule that identifies an interaction (non-redundant interaction) and a designated biological phenomenon.
FIG. 16 is a flowchart of a relation strength calculating/displaying process.

FIG. 15 is a diagram for explaining the relation strength S2 between a molecule that identifies an interaction (non-redundant interaction) and a designated biological phenomenon. As depicted in FIG. 15, each corresponding color is determined according to the magnitude of the relation strength S2. The corresponding color is coloring applied to an edge (arrow) that represents an interaction of the molecular network 510.

The relation strength S1 with an interaction may be weak and no specificity may appear while the relation strength S2 for a molecule may be strong and specificity may appear. In this case, by correcting the relation strength S1 using the relation strength S2, involvement of the molecule in the designated biological phenomenon may be emphasized. This correction is expressed by, for example, Equations (6) and (7).

$$S1' = S1 \times w1 + S2av \times w2 \tag{6}$$

$$S2av = (S2A + S2B)/2 \tag{7}$$

"S1'" is the relation strength obtained after the correction of the relation strength S1. "w1" is a weight for the relation strength S1. "w2" is a weight for the relation strength S2av. "w1" and "w2" are set in advance.

"S2A" is the relation strength between the molecule A of the molecule pair of interest and the designated biological phenomenon. "S2B" is the relation strength between the molecule B of the molecule pair of interest and the designated biological phenomenon. "S2av" is the average value of the relation strength S2A and the relation strength S2B.

For example, the relation strength S1 of the molecule pair including the molecules A (protein P5) and B (protein P2) depicted in FIG. 13 is "1.33" that is a low value while the relation strength S2 of the molecule A (protein P5) depicted in FIG. 15 is "9.14" and the relation strength S2 of the molecule B (protein P2) depicted in FIG. 15 is "28.35", which are higher values than that of the relation strength S1.

Assuming that the weight w1 is w1=0.8 and the weight w2 is w2=0.2 and these values substitute in the above Equations (6) and (7), the relation strength S1' after the correction is S1'=4.813 and the relation strength may be corrected to be a value higher than the value before the correction. Therefore, in a retrieval process described later, by considering that the route to the molecule is also involved in the disorder, the priority of the route at retrieval may be raised.

The display control unit 1104 in FIG. 11 has a function of displaying the molecular network 510 by controlling the display screen 500 as depicted in FIG. 12. The display control unit 1104 may further display the molecular network 510 by applying, to each edge representing an interaction and each node representing a molecule as depicted in FIG. 14, a corresponding color that corresponds to the relation strength S1 or the relation strength S2.

The display control unit 1104 may further display emphasizing the number of times of concurrency with the designated biological phenomenon (that is, for example, the number of reference IDs depicted in FIG. 13). Thereby, whether each molecule pair of interest is confirmed for the designated biological phenomenon may be grasped at a glance. In the molecular network 510 depicted in FIG. 14, a portion of the designated biological phenomenon where "Drug1" significantly fluctuates is displayed with emphasis.

For example, an edge connection is red when the relation strength S1 is 10 points or higher and the concurrency count is five counts or higher; pink when the relation strength S1 is five points or higher; blue when the relation strength S1 is three points or higher; gray for those that are present even when the concurrency count is one; and black when the relation strength S2 is lower than two points. These conditions are changeable using a graphical interface and thus, when values of the relation strength S1 are substantially equivalent, the relation for a user to note may be indicated by changing a score index.

Prior to description of the selecting unit 1105 and the retrieving unit 1106, a relation strength calculating/displaying process procedure will be described. FIG. 16 is a flowchart of the relation strength calculating/displaying process procedure. As depicted in FIG. 16, the name of the biological phenomenon is input into the input column 1201 by user operation as depicted in FIG. 12 and thereby, the designating unit 1101 receives the designation of the biological phenomenon (step S1601).

Waiting occurs until detection of a clicking of the application button 1202 (step S1602: NO). When the clicking has been detected (step S1602: YES), the extracting unit determines whether any unprocessed (non-redundant) interaction whose relation strength S has not been calculated is present in the molecular network 510 (step S1603).

If an unprocessed interaction is present (step S1603: YES), the interaction is extracted (step S1604). The calculating unit 1103 calculates the relation strength S1 between the designated biological phenomenon and the interaction extracted (step S1605) and the procedure returns to step S1603.

If no unprocessed interaction is present at step S1603 (step S1603: NO), edges of the molecular network 510 are displayed emphasized according to the relation strength calculated for each interaction (step S1606).

Each edge is displayed emphasized according to the relation strength S1 thereof with the interaction as above and thereby, whether each interaction is confirmed for the designated biological phenomenon may be grasped at a glance. The relation strength S1 with the interaction is dependent on the number of medical references reported and thus, providing an advantage in that a popular relation is visualized. However, the procedure is a statistical approach and thus, the original mechanism may not be visualized.

To cover such a case, by correcting the relation strength S1 with the interaction using the relation strength S2 with the molecule, considering that the route to the molecule is also involved in the disorder, the priority at retrieval may be raised. Thereby, clues for a user to construct a hypothesis for an experiment may be increased without any experimental data.

The selecting unit 1105 and the retrieving unit 1106 depicted in FIG. 11 will be described. The selecting unit 1105 has a function of receiving selection of a molecule that is a starting node from among the nodes constituting the molecular network 510. More specifically, for example, the standard molecular notation of the molecule that is the starting node is input by user operation into the input column 1401 for the staring molecule in the mapping screen 1400 depicted in FIG. 14 and, thereby, the selecting unit 1105 receives the selection of the starting molecule.

FIG. 17 is a diagram for explaining the mapping screen 1400 after receipt of the selection of the molecule that is the starting node. In FIG. 17 (in also FIG. 14), an asterisk represents a known biological phenomenon. As to a known biological phenomenon, by accessing the pharmacological DB 400 using, as a key, the ID of a gene or a protein whose cause-and-effect relation with the designated biological phenomenon has been confirmed, whether any known biological phenomenon occurs may be determined.

For example, when information indicating that "a gene (DNA1) is overexpressed in non-insulin-dependent diabetes mellitus" is stored in the pharmacology DB 400, it becomes clear that a known biological phenomenon occurs at a node for the standard molecular notation "DNA1" in the molecular network 510. Therefore, an asterisk is displayed in the vicinity of the node.

The retrieving unit 1106 has functions of retrieving a route from the starting node to the node at which the known biological phenomenon occurs and outputting a retrieval result 1110. The retrieving unit 1106 follows the directions of edges (arrows) that represent interactions to retrieve a route. When an edge branches to two or more edges, a branched edge having a larger value of the relation strength S1 is selected with higher priority.

In this case, the calculating unit 1103 further calculates relation strength S3 for the retrieved route. The relation strength S3 between a biological phenomenon and a retrieved route may be calculated from the harmonic average, the arithmetic average, and the geometric average of the relation strength S1 of the interactions being sought. By using the harmonic average of these averages, influence by an interaction having extraordinary relation strength S3 is suppressed and therefore, each interaction may be respected. Therefore, the selection matches this problem.

The relation strength S3 may be calculated according to Equation (8).

$$S3 = \frac{N}{\sum_{a=1}^{N} \frac{g(a)}{f(a)}} \quad (8)$$

In Equation (8), "f(a)" is a function based on the relation strength S2 between an interaction and a designated biological phenomenon, and a common logarithm thereof may be taken or those values under a threshold may be eliminated by setting the threshold value. "N" is the number of interactions in a retrieved route. That is, a value obtained by subtracting one from the number of nodes on the retrieved route.

"g(a)" is a function expressing the presence or absence of direct bonding and takes a value that is 0<g(a)≤1. For example, g(a) is g(a)=1 when direct bonding is present and g(a) is g (a)=0.7 when direct bonding is not confirmed or is confirmed for a domain. g(a) is g(a)=0.5 when no direct bonding is reported. g(a) is g(a)=0.3 when it is known that no direct bonding is present.

FIG. 18 is a diagram for explaining the retrieval result 1110 by the retrieving unit 1106. As depicted in FIG. 18, the standard molecular notation and the molecule type of the starting node, the standard molecular notation and the molecule type of the ending node (the node at which a biological phenomenon occurs), the retrieved routes, and the relation strength S3 may be obtained for each of (the route IDs of) the retrieved routes as the retrieval result 1110.

As depicted in FIG. 18, the relation strength S3 of the designated biological phenomenon is calculated for each of the retrieved routes and the result is sorted to obtain a sorted result 1800. Therefore, the retrieved routes that are closely related to the designated biological phenomenon may be selected with priority. Thereby, for the disorder, routes that are appropriate from the standpoint of the user may be extracted. Therefore, an increase in the speed of the research for innovative drug development may be realized.

Through the display control unit 1104, edges may be displayed emphasized in descending order of the relation strength S3 thereof and the retrieved routes that each have high relation strength S3 may be displayed by the clicking of a button by the user. FIG. 19 is a diagram for explaining the mapping screen 1400 that displays the retrieved routes (Part I). A retrieved route R1 is the retrieved route (route ID: 003) ranked as 1, as depicted in FIG. 18.

When a Next button 1701 is clicked, the retrieved route of the subsequent rank (rank 2) is displayed. FIG. 20 is another diagram for explaining the mapping screen 1400 that displays the retrieved routes (Part II). A retrieved route R2 is the retrieved route (route ID: 006) ranked 2, as depicted in FIG. 18. When the Next button 1701 is clicked, the retrieved route of the subsequent rank (rank 3) is displayed. On the other hand, when a Prev button 2001 is clicked, the retrieved route that is one rank higher is displayed.

It has been described that the calculating unit 1103 calculates the relation strength S3 of a retrieved route according to Equation (8) using the interaction and the relation strength S1. However, a calculation equation that supplementally utilizes the relation strength S2 with each node as the weight thereof may be used, such as Equation (9).

$$S3 = \frac{N}{\sum_{a=1}^{N} \frac{g(a) \cdot h(a)}{f(a)}} \quad (9)$$

In Equation (9), "h(a)" is calculated using the arithmetic average, the geometric average, or the harmonic average, etc., of the relation strength S2 with an object molecule. The result obtained by taking a common logarithm of h(a) may be used as h(a). In this case, even when the relation strength S1 with an interaction is not high, if the relation strength S2 with the molecule is high, the probability that the retrieved routes of the molecule pair of interest are selected is increased.

FIG. 21 is a diagram for explaining a sorted result 2100 obtained by sorting the retrieval result 1110 by the retrieving unit 1106. As depicted in FIG. 21, the retrieval result 1110 is sorted based on the relation strength S3 calculated according to Equation (9).

Figure 23:
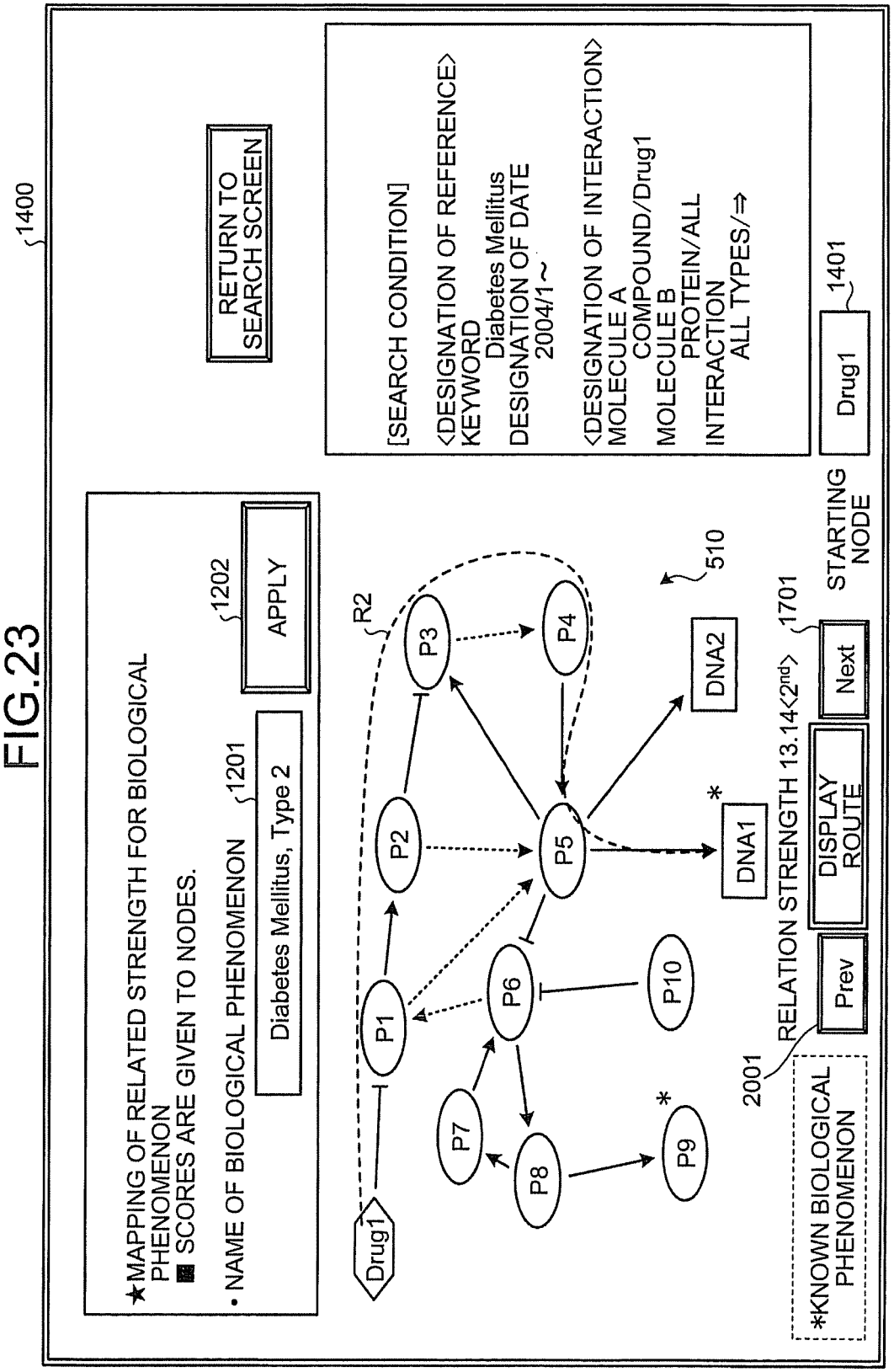
FIG. 23 is another diagram for explaining the mapping screen 1400 that displays the retrieved routes (Part IV)

FIG. 22 is another diagram for explaining the mapping screen 1400 that displays the retrieved routes (Part III). The retrieved route R1 is the retrieved route (route ID: 006) ranked 1, as depicted in FIG. 21. FIG. 23 is another diagram for explaining the mapping screen 1400 that displays the retrieved routes (Part IV). A retrieved route R2 is a retrieved route (route ID: 003) ranked 2, as depicted in FIG. 21.

Figure 24:
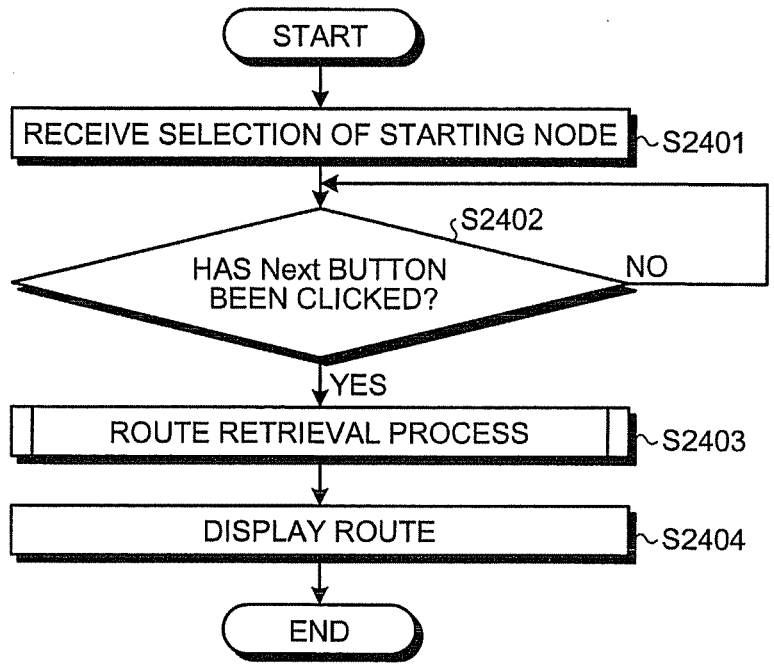
FIG. 24 is a flowchart of a starting node selection/route retrieval process.

A starting node selection/route retrieval process will be described. FIG. 24 is a flowchart of the starting node selection/route retrieval process. As depicted in FIG. 24, the selecting unit 1105 receives the selection of the molecule that is the starting node via a user input of the name of the molecule that is the starting node into the input column 1201 as depicted in FIG. 12 (step S2401).

Waiting occurs until clicking of the Next button 1701 is detected (step S2402: NO). When the clicking of the Next button 1701 has been detected (step S2402: YES), the retrieving unit 1106 executes a route retrieval process (step S2403).

Thereafter, as depicted in FIGS. 19, 20, 22, and 23, the display control unit 1104 displays on the display screen 500 the retrieved routes together with the molecular network 510 (step S2404). At step S2404, the retrieved route having the highest relation strength is displayed first and thereafter, the retrieved routes are sequentially displayed in response to clicking of the Next button 1701 and the Prev button 2001.

Figure 25:
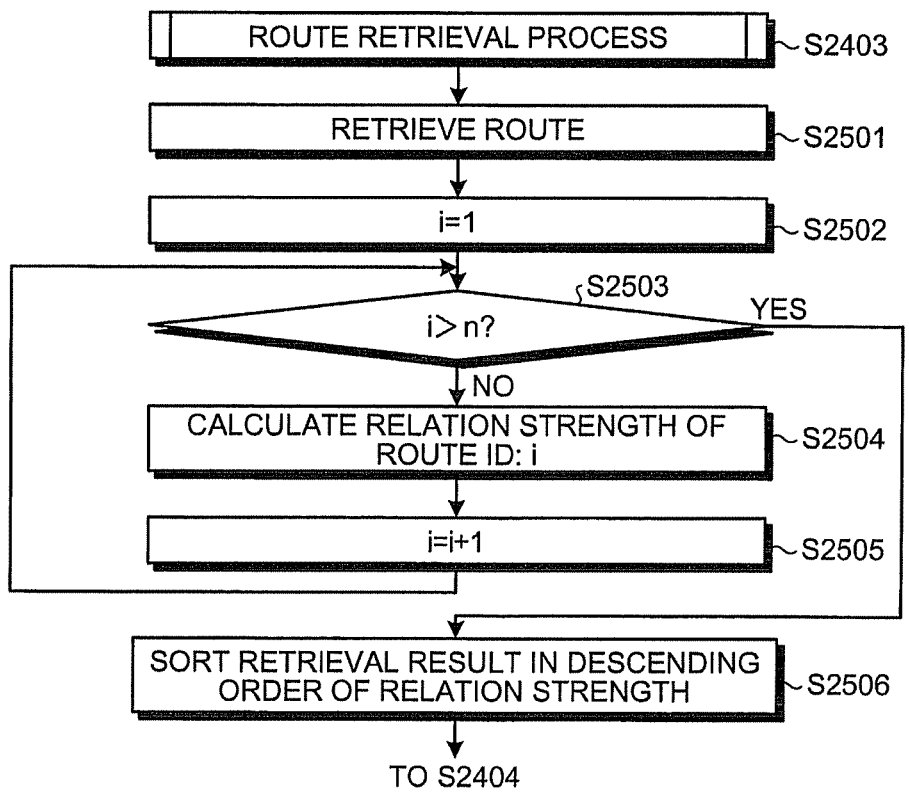
FIG. 25 is a flowchart of a route retrieval process (step S2403)

Details of the route retrieval process depicted at step S2403 will be described. FIG. 25 is a flowchart of the route retrieval process (step S2403). As depicted in FIG. 25, retrieval is executed to cover all the routes with the starting node and the ending node being set in advance (step S2501). Route IDs: i (i=1, 2, ..., n) are allocated to the retrieved routes.

Assuming that the number of retrieved routes is n, the route ID: i is set to be i=1 (step S2502) and whether i is i>n is determined (step S2503). If i is not i>n (step S2503: NO), the calculating unit 1103 calculates the relation strength S3 of the route ID: i (step S2504). "i" is incremented by one (step S2505) and the procedure returns step S2503.

On the other hand, if i is i>n at step S2503 (step S2503: YES), the retrieval result 1110 is sorted in descending order of relation strength S3 as depicted in FIG. 18 (step S2506). Thereafter, the procedure moves to step S2404.

In this manner, the relation strength S3 of the designated biological phenomenon is calculated for each of the retrieved routes and the retrieval result 1110 is sorted. Thereby, the retrieved routes that closely relate to the designated biological phenomenon may be selected with priority, disorder routes that are appropriate from the standpoint of the user may be extracted from the molecular network 510, and the speed of the research for innovative drug development may be increased.

Another example of the route retrieval will be described. The above route retrieval process by the retrieving unit 1106 is useful for grasping the routes that are popular when a designated biological phenomenon is handled. However, in this example, a molecular pair or a retrieved route that is new and that has not been studied much by the user is created.

More specifically, for example, a detecting function of detecting unstable interactions among the interactions constituting a retrieved route and a creating function of creating the molecular network 510 after direction reversal that reverses the direction of each of the unstable interactions detected are added. Thereby, a molecular pair or a retrieved route that is new and that has not been studied much by the user may be created.

As to an "unstable interaction", when a non-redundant interaction is determined by a narrow margin in the set of interactions, the non-redundant interaction is an "unstable interaction". For example, when the difference between the number of the reference IDs of the references having described therein that the direction of an interaction is one direction and the number of the reference IDs of the references having described therein that the direction of the interaction is the other direction is within a predetermined value, the interaction is an unstable interaction. Therefore, the direction determined by making a decision by majority is reversed and a new molecular network 510 is created.

Figure 26:
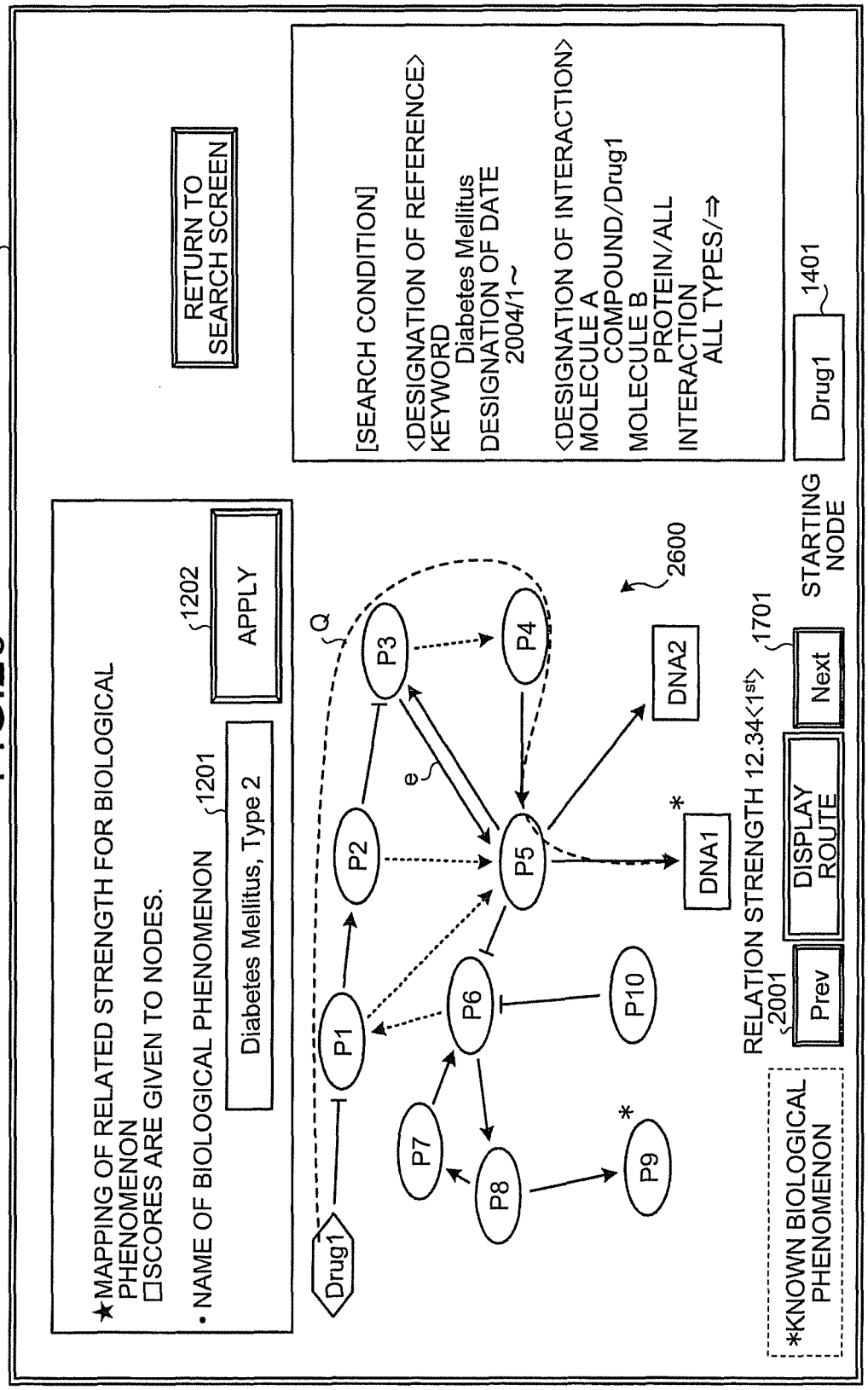
FIG. 26 is a diagram for explaining the molecular network 510 after reversing the direction of the interaction.

FIG. 26 is a diagram for explaining the molecular network 510 after reversing the direction of the interaction. As depicted in FIG. 26, a molecular network 2600 whose direction of the interaction between molecules P5 and P3 of the molecule pair is reversed is created and is displayed on the mapping screen 1400. A retrieved route Q is a retrieved route that is newly retrieved by this direction reversal. Thereby, the interaction (edge "e") after the direction reversal and the retrieved route Q thereof may be created.

Figure 27:
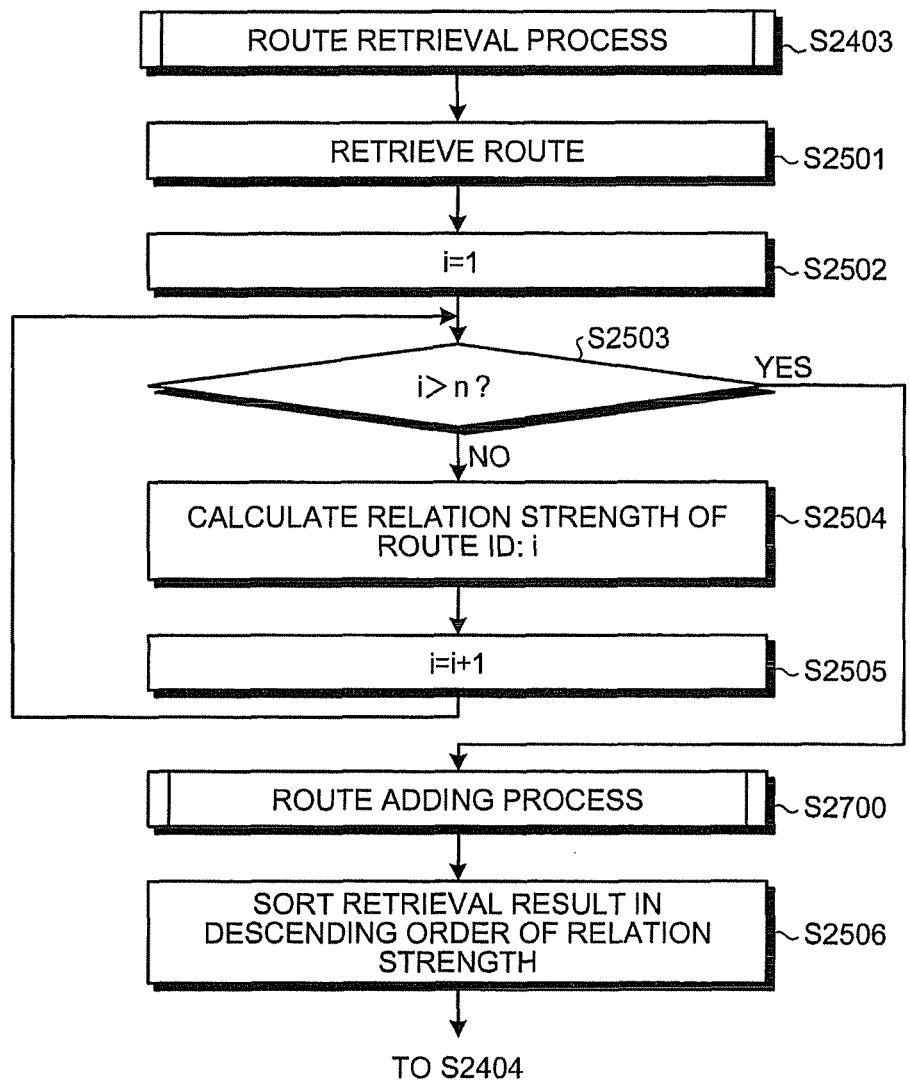
FIG. 27 is a flowchart of a route retrieval process that includes a route adding process.

The route retrieval process in this case will be described. FIG. 27 is a flowchart of a route retrieval process that includes a route adding process. The processes identical to those depicted in FIG. 25 are given the same numerals used in FIG. 25 and the description therefor is omitted. As depicted in FIG. 27, the route adding process is executed between "step S2503: YES" and "step S2506" (step S2700).

Figure 28:
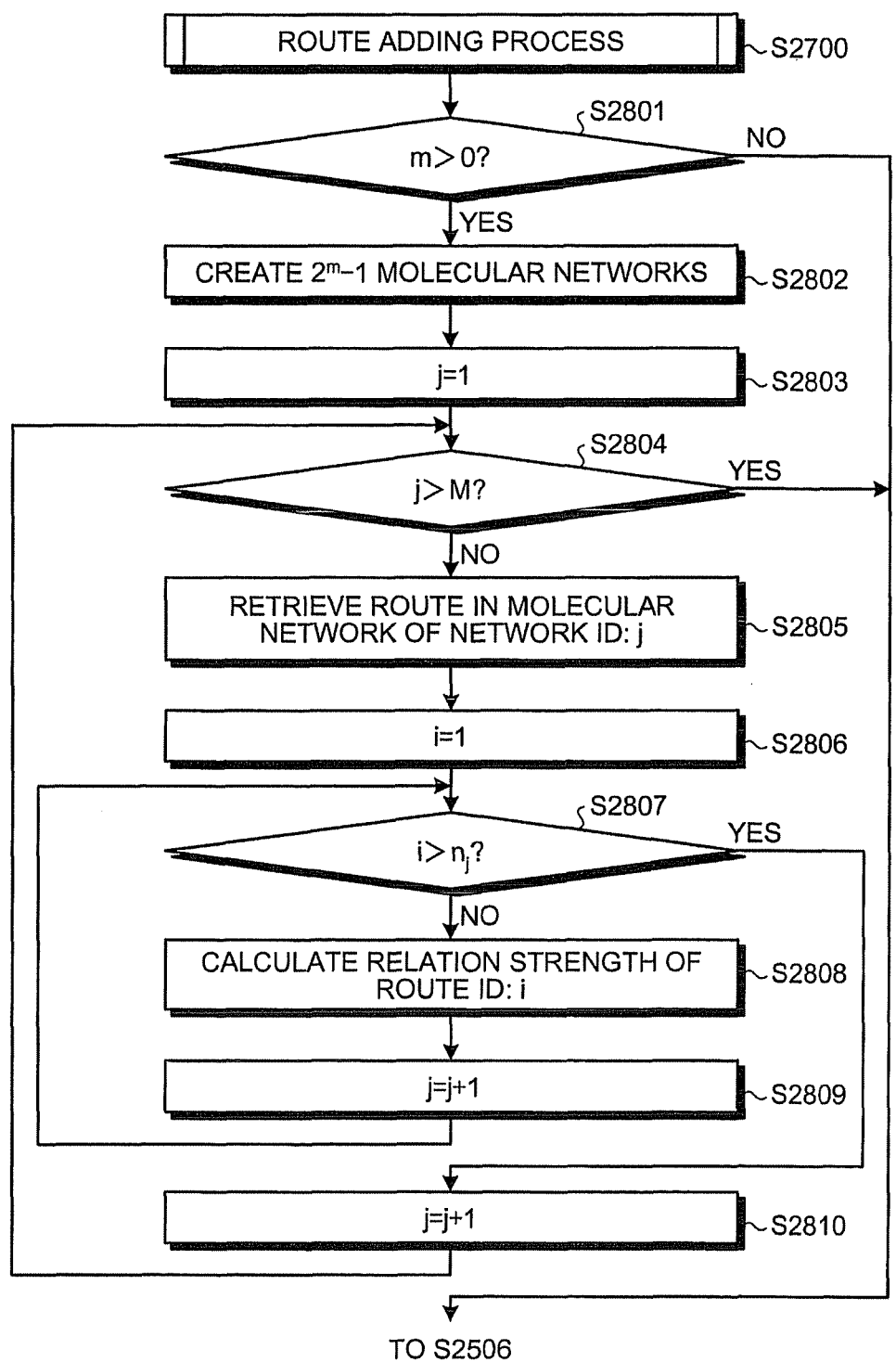
FIG. 28 is a flowchart of the route adding process (step S2700)
Figure 29:
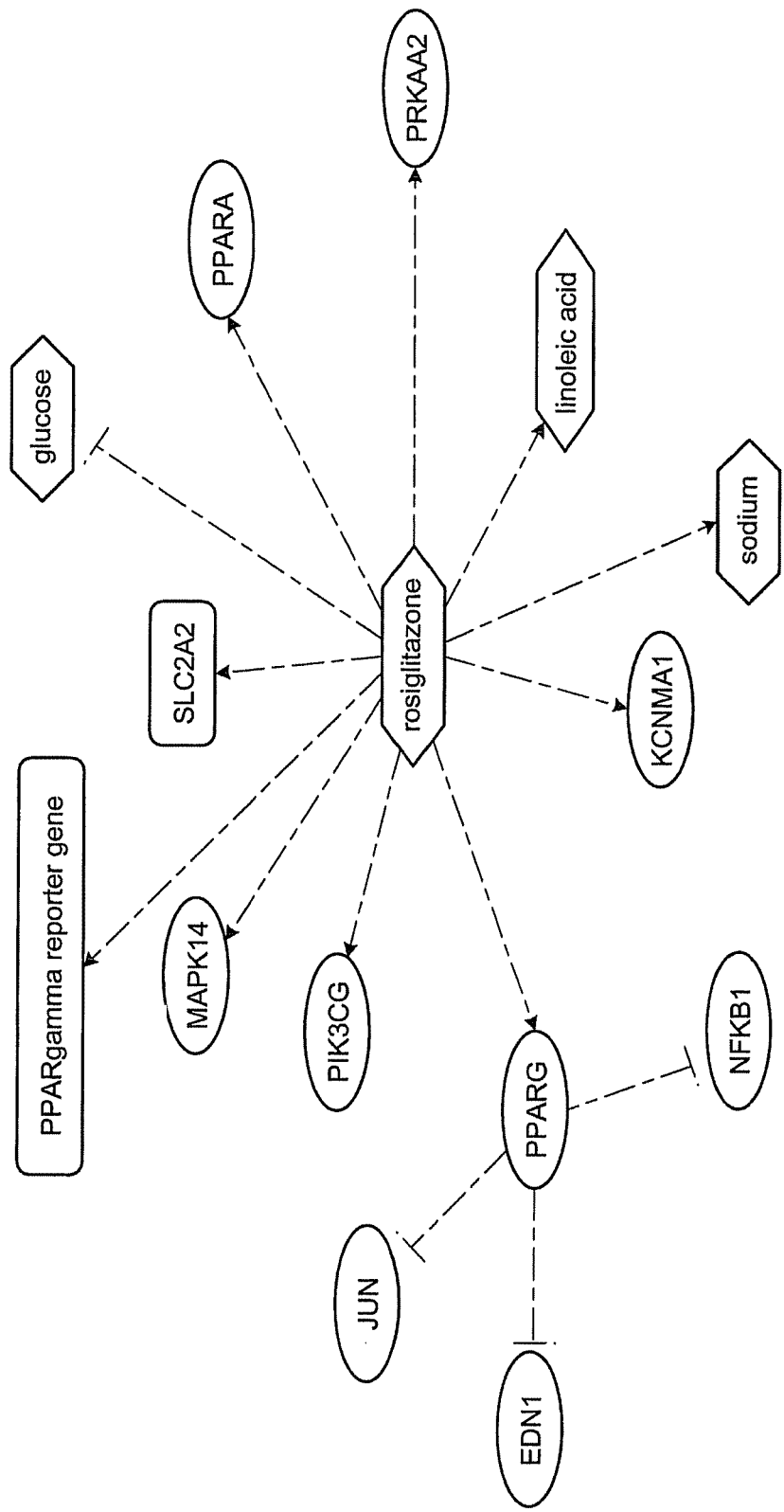
FIG. 29 is a schematic of pathways.
Figure 30:
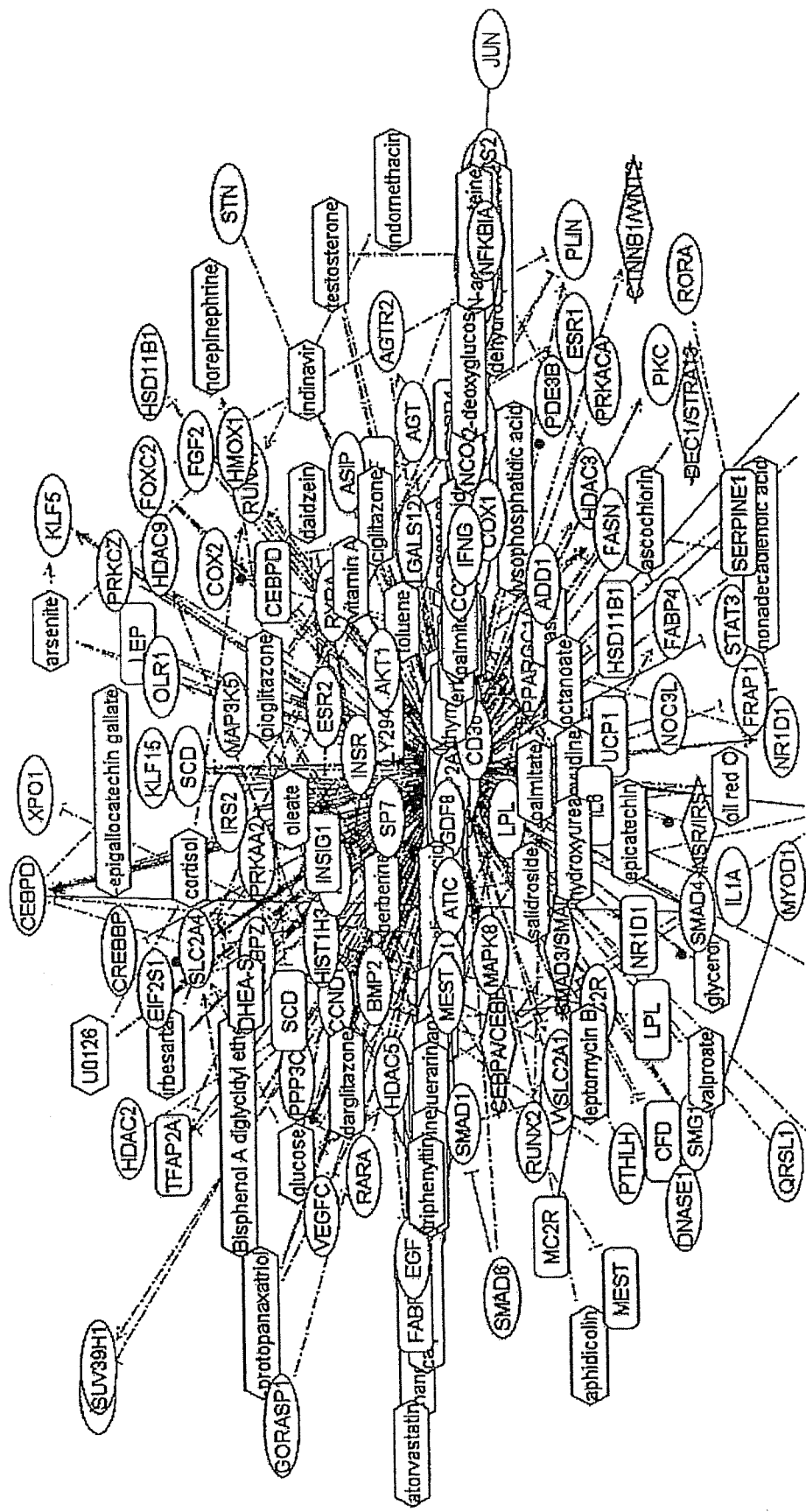
FIG. 30 is a schematic depicting an extensive network for which selection of a route is difficult.

FIG. 28 is a flowchart of the route adding process (step S2700). Whether any unstable interaction has been detected among the interactions constituting the molecular network 510 is determined (step S2801). That is, when the number of unstable interactions is "m", whether m is m>0 is determined. If m is not m>0 (step 2801: NO), no unstable interaction is present and therefore, the procedure moves to step S2506.

On the other hand, if m is m>0 (step S2801: YES), M (M=2m−1) types of molecular network 510 are created (step S2802). Network IDs: j (j=1, 2, ..., M) are allocated to the newly created M molecular networks 510.

The network ID: j is set to be j=1 (step 2803) and whether j is j>M is determined (step S2804). If j is not j>M (step S2804: NO), the route retrieval is executed in the molecular network 510 of the network ID: j (step S2805). Route IDs: i (i=1, 2, ..., n) are allocated to the retrieved routes.

The route ID: i is set to be i=1 (step S2806) and whether is i>n is determined (step S2807). If i is not i>n (step S2807: NO), the calculating unit 1103 calculates the relation strength S3 of the route ID: i (step S2808). Thereafter, the route ID: i is incremented by one (step S2809) and the procedure returns to step S2807.

On the other hand, if i is i>n (step S2807: YES), the network ID: j is incremented by one (step S2810) and the procedure returns to step S2804. When j is j>M at step S2804 (step S2804: YES), the route retrieval for all the molecular networks 510 comes to an end and the procedure moves to step S2506.

In this manner, by detecting unstable interactions and reversing their directions, a molecular pair or a retrieved route that is new and has not been studied much by the user is created.

The method of calculating the relation strength between an interaction and an biological phenomenon in the above embodiment is also used for sequence analysis of genes. However, "a group of MeSH terms given to the medical references" and "interactions" are set to be calculated in the embodiment being different from the sequence analysis of genes. Thereby, the medical and biological meanings that the MeSH terms have may be numerically given to the "interactions". Therefore, each of the links between the interactions and the designated in vivo phenomena may be expressed visually in the molecular network 510 and this has been unable to be realized.

A value having a medical or biological meaning for an interaction is given as the relation strength and therefore, a retrieved route that has a deep relation with a specific biological phenomenon may mechanically be selected from a pathway.

The relation strength with a medical or biological meaning is given to each of the interactions in a pathway and therefore, route retrieval that is not obtained by conventional approaches is enabled and new in vivo phenomena may be considered.

Pathways that are complicated and diversely diverge may be simplified using the retrieved routes and therefore, the number of references describing therein the interactions that are the components of the pathway is also reduced. Therefore, the number of references to be read when the details of the medical and biological meanings of the routes selected are confirmed, may be reduced.

The mechanical route selection for the pathway is enabled by statistically processing, using data mining, the terms having medical and biological meanings, i.e., so-called MeSH terms described in a tremendous number of medical references and giving the statistical values to the pathway. Such mechanical processing on the tremendous number of medical references cannot be executed using manual curation described in "BACKGROUND". Therefore, the medical and biological meanings obtained by the embodiment may lead to quite novel discoveries that lie beyond the realm of fixed ideas formed by the experiences of a person.

Unlike curation, the relation strength having a medical or biological meaning is mechanically converted into a score and is given to each of interactions and molecules in a pathway. Therefore, even when addition and/or updating of data concerning the medical references such as PubMed used for the calculation are/is executed, this may be coped with immediately and mechanically. By doing so, the state of updating of medical references to which researchers contribute may immediately be reflected on a pathway, fixation of the medical and biological meanings that the pathway has may be prevented, and updating of the pathway corresponding to the state of research may be facilitated.

Drawing of and route retrieval for the pathway are enabled based on the interactions obtained from the existing medical references and therefore, a user (researcher) may consider a phenomenon having medical and biological meanings and may find a new subject of study, i.e., may create a hypothesis, without conducting any experiments by him/herself.

As described, according to the embodiment, by estimating molecular interactions that closely relate to a disorder, routes having biological meanings may be efficiently obtained from among a tremendous number of routes. Therefore, creation of a hypothesis of and consideration for an in vivo mechanism may efficiently be executed and therefore, the load on the researchers may be reduced in pharmaceutical companies and academic institutions.

Not only reduction of the load, but also new discoveries may be facilitated for the researchers. Obsolescence of findings due to the advancement of research and a change in the times may be prevented by continuously providing the researchers with pathways that reflect new knowledge.

The molecular network analysis support method explained in the present embodiment may be implemented by a computer, such as a personal computer and a workstation, executing a program that is prepared in advance. The program is recorded on a computer-readable recording medium such as a hard disk, a flexible disk, a CD-ROM, an MO, and a DVD, and is executed by being read out from the recording medium by a computer. The program may be distributed through a network such as the Internet.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A molecular network analysis support method performed by a molecular network analysis support apparatus, the analysis support method comprising:

receiving, through a user input, a designated name of a biological phenomenon;

extracting, from a molecular network including nodes representing molecules and edges between the nodes representing molecular interactions between the molecules, information indicating a type of molecular reaction;

calculating, using the molecular network analysis support apparatus with reference to a first database storing information on a plurality of medical references, a first score and a second score, the first score being a ratio of a number of the plurality of medical references in which both the designated name of the biological phenomenon and the information indicating the type of molecular reaction appear for a molecular pair in relation to a number of the plurality of medical references in which the molecular pair appears, and the second score being a ratio of a number of the plurality of medical references in which both the designated name of the biological phenomenon and the information indicating the type of molecular reaction appear for all molecular pairs of the molecular network in relation to a number of the plurality of medical references in which all of the molecular pairs appear;

calculating, using the molecular network analysis support apparatus, a value of a first relation strength for each interaction of the molecular pair in the molecular network based on an operation using ratios of the first score and the second score, each value of the first relation strength representing a strength of a relationship between the biological phenomenon identified by the designated name of the biological phenomenon and the type of molecular interaction for the molecular pair; and controlling a display screen to display the molecular network in which the value of the first relation strength for an interaction of the molecular pair is correlated with at least a corresponding edge and a corresponding node.

2. The molecular network analysis support method according to claim 1, comprising:

calculating, using the molecular network analysis support apparatus with reference to the database, a third score for each molecule of the molecular pair, the third score being a ratio of a number of medical references of the plurality of medical references in which both the designated name of the biological phenomenon and the information indicating the type of molecular interaction involving the molecule appear in relation to a number of medical references of the plurality of medical references in which the molecule appears;

calculating a second relation strength for each molecule of the molecular pair, each value of the second relation strength representing a strength of a relationship between the biological phenomenon identified by the designated name and the type of molecular interaction involving the molecule; and correcting the values of the first relation strength for the molecular pair using respective calculated values of the second relation strength.

3. The molecular network analysis support method according to claim 1, wherein the controlling includes displaying the molecular network in which values of the first and second relation strength are respectively correlated with corresponding edges and nodes.

4. The molecular network analysis support method according to claim 3 comprising:

receiving, through user input, selection of a starting node from among the molecular network; and retrieving, from the molecular network, a route from the selected starting node to a node at which a known biological phenomenon occurs, wherein when an edge branches into two or more branched edges, the branched edge correlated with a larger value of the first relation strength is selected for the route, wherein a node at which the biological phenomenon occurs is determined with reference to a second database storing names of molecules and related descriptions of known biological phenomena, and wherein the controlling includes controlling the display screen to display the retrieved route.

5. The molecular network analysis support method according to claim 4 further comprising:

detecting, with reference to the first database, an edge representing an unstable interaction from among edges representing interactions constituting the retrieved route, the unstable interaction being detected when a difference between a number of medical references of the plurality of medical references in which information indicating a type of interaction having one direction appears in relation to a number of medical references of the plurality of medical references in which information indicating a type of interaction having an opposite direction appears, is within a predetermined range; and creating a molecular network after direction reversal that reverses direction of the detected edge representing the unstable interaction, wherein the retrieving includes retrieving, from the molecular network created after the direction reversal, a route from a starting node to the node at which the biological phenomenon occurs, the route passing through the edge representing the unstable interaction whose direction has been reversed, and the controlling includes controlling the display screen to display the retrieved route.

6. The molecular network analysis support method according to claim 4, comprising:

calculating a value of a third relation strength representing a strength of a relationship between the biological phenomenon and the retrieved route, the value of the third relation strength calculated based on an average of values of the first relation strength determined for edges constituting the route, and wherein the controlling includes controlling the display screen to display the retrieved route, based on the calculated value of the third relation strength.

7. A molecular network analysis support apparatus comprising:

a memory; and at least one processor connected with the memory, which receives, through a user input, a designated name of a biological phenomenon, extracts, from a molecular network including nodes representing molecules and edges between the nodes representing molecular interactions between the molecules, information indicating a type of molecular reaction, calculates, with reference to a first database storing information on a plurality of medical references, a first score and a second score, the first score being a ratio of a number of medical references of the plurality of medical references in which both the designated name of the biological phenomenon and the information indicating the type of molecular reaction appear for a molecular pair in relation to a number of medical references of the plurality of medical references in which the molecular pair appears, and the second score being a ratio of a number of medical references of the plurality of medical references in which both the designated name of the biological phenomenon and the information indicating the type of molecular reaction appear for all molecular pairs of the molecular network in relation to a number of medical references of the plurality of medical references in which all of the molecular pairs appear, calculates a value of a first relation strength for each interaction of the molecular pair in the molecular network based on an operation using ratios of the first score and the second score, each value of the first relation strength representing a strength of a relationship between the biological phenomenon identified by the designated name of the biological phenomenon and the type of molecular interaction for the molecular pair; and controls a display screen to display, the molecular network in which the value of the first relation strength for an interaction of the molecular pair is correlated with at least a corresponding edge and a corresponding node.

8. The molecular network analysis support apparatus according to claim 7, wherein a third score is calculated for each molecule of the molecular pair, the third score being a ratio of a number of medical references of the plurality of medical references in which both the designated name of the biological phenomenon and the information indicating the type of molecular interaction involving the molecule appear in relation to a number of medical references in which the molecule appears, a value of a second relation strength is calculated for each molecule of the molecular pair based on a function including a ratio of the third score for the molecule in relation to the second score for the molecular pair, each value of the second relation strength representing a strength of a relationship between the biological phenomenon identified by the designated name and a type of molecular interaction involving the molecule, and the values of the first relation strength for the molecular pair are corrected; using respective calculated values of the second relation strength.

9. The molecular network analysis support apparatus according to claim 7, wherein the display screen is controlled to display the molecular network wherein the controlling includes displaying the molecular network in which values of the first and second relation strength are respectively correlated with corresponding edges and nodes.

10. The molecular network analysis support apparatus according to claim 9, wherein the at least one processor
receives, through user input, selection of a starting node from among the molecular network; and
retrieves, from the molecular network, a route from the selected starting node to a node at which a known biological phenomenon occurs,
wherein the display screen is controlled to display the retrieved route.

11. The molecular network analysis support apparatus according to claim 10, wherein the at least one processor
detects, with reference to the first database, an edge representing an unstable interaction from among edges representing interactions constituting the retrieved route, the unstable interaction being detected when a difference between a number of medical references of the plurality of medical references in which information indicating a type of interaction having one direction appears in relation to a number of medical references of the plurality of medical references in which information indicating a type of interaction having an opposite direction appears, is within a predetermined range; and
creates a molecular network after direction reversal that reverses direction of the detected edge representing the unstable interaction,
wherein a route from a starting node to the node at which the biological phenomenon occurs is retrieved from the molecular network created after the direction reversal, the route passing through the edge representing the unstable interaction whose direction has been reversed, and
the display screen is controlled to display the retrieved route.

12. The molecular network analysis support apparatus according to claim 10, wherein
a value of a third relation strength is calculated, the value of the third relation strength representing a strength of a relationship between the biological phenomenon and the retrieved route, the value of the third relation strength calculated based on an average of values of the first relation strength determined for edges constituting the route, and
the display screen is controlled to display the retrieved route, based on the calculated value of the third relation strength.

13. A non-transitory computer-readable recording medium storing therein a molecular network analysis support program that causes a computer to execute a process comprising:
receiving, through a user input, a designated name of a biological phenomenon;
extracting, from a molecular network including nodes representing molecules and edges between the nodes representing molecular interactions between the molecules, information indicating a type of molecular reaction;
calculating, with reference to a first database storing information on a plurality of medical references, a first score and a second score, the first score being a ratio of a number of medical references of the plurality of medical references in which both the designated name of the biological phenomenon and the information indicating the type of molecular reaction appear for a molecular pair in relation to a number of medical references of the plurality of medical references in which the molecular pair appears, and the second score being a ratio of a number of medical references of the plurality of medical references in which both the designated name of the biological phenomenon and the information indicating the type of molecular reaction appear for all molecular pairs of the molecular network in relation to a number of medical references of the plurality of medical references in which all of the molecular pairs appear;
calculating a value of a first relation strength for each interaction of the molecular pair in the molecular network based on an operation using ratios of the first score and the second score, each value of the first relation strength representing a strength of a relationship between the biological phenomenon identified by the designated name of the biological phenomenon and the type of molecular interaction for the molecular pair; and
controlling a display screen to display the molecular network in which the value of the first relation strength for an interaction of the molecular pair is correlated with at least a corresponding edge and a corresponding node.

14. The non-transitory computer-readable recording medium according to claim 13, wherein the process comprising:
calculating a third score for each molecule of the molecular pair, the third score being a ratio of a number of medical references of the plurality of medical references in which both the designated name of the biological phenomenon and the information indicating the type of molecular interaction involving the molecule appear in relation to a number of medical references in which the molecule appears,
calculating a value of a second relation strength for each molecule of the molecular pair based on a function including a ratio of the third score for the molecule in relation to the second score for the molecular pair, each value of the second relation strength representing a strength of a relationship between the biological phenomenon identified by the designated name and a type of molecular interaction involving the molecule, and
wherein the values of the first relation strength for the molecular pairs are corrected using respective calculated values of the second relation strength.

15. The non-transitory computer-readable recording medium according to claim 13, wherein the controlling of the process comprises:
displaying the molecular network in which values of the first and second relation strength are respectively correlated with corresponding edges and nodes.

16. The non-transitory computer-readable recording medium according to claim 15 wherein the process comprises:
receiving, through user input, selection of a starting node from among the molecular network; and
retrieving, from the molecular network, a route from the selected starting node to a node at which a known biological phenomenon occurs,
wherein the display screen is controlled to display the retrieved route.

17. The non-transitory computer-readable recording medium according to claim 16,wherein the process comprises:
detecting, with reference to the first database, an edge representing an unstable interaction from among edges representing interactions constituting the retrieved route, the unstable interaction being detected when a difference between a number of medical references of the plurality of medical references in which information indicating a type of interaction having one direction appears in relation to a number of medical references of the plurality of medical references in which information indicating a type of interaction having an opposite direction appears, is within a predetermined range; and creating a molecular network after direction reversal that reverses direction of the detected edge representing the unstable interaction, wherein a route from a starting node to the node at which the biological phenomenon occurs is retrieved from the molecular network created after the direction reversal, the route passing through the edge representing the unstable interaction whose direction has been reversed, and the display screen is controlled to display the retrieved route.

18. The non-transitory computer-readable recording medium according to claim 16, wherein the process comprises:

calculating a value of a third relation strength is calculated, the value of the third relation strength representing a strength of a relationship between the biological phenomenon and the retrieved route, wherein the value of the third relation strength is calculated based on an average of values of the first relation strength determined for edges constituting the route, and the display screen is controlled to display the retrieved route in accordance with the calculated value of the third relation strength.

* * * * *

UNITED STATES PATENT AND TRADEMARK OFFICE
CERTIFICATE OF CORRECTION

PATENT NO.       : 8,818,732 B2
APPLICATION NO.  : 12/508039
DATED            : August 26, 2014
INVENTOR(S)      : Shuhei Kinoshita et al.

Page 1 of 1

It is certified that error appears in the above-identified patent and that said Letters Patent is hereby corrected as shown below:

In the Claims

Column 22, line 38, in claim 7 delete "display," and insert -- display --, therefor.

Column 22, line 62, in claim 8 delete "corrected;" and insert -- corrected --, therefor.

Signed and Sealed this
Eighteenth Day of November, 2014

Michelle K. Lee
*Deputy Director of the United States Patent and Trademark Office*